(12) United States Patent
Yamanaka et al.

(10) Patent No.: US 10,519,425 B2
(45) Date of Patent: Dec. 31, 2019

(54) HIGHLY EFFICIENT METHOD FOR ESTABLISHING INDUCED PLURIPOTENT STEM CELL

(71) Applicant: Kyoto University, Kyoto-shi, Kyoto (JP)

(72) Inventors: Shinya Yamanaka, Kyoto (JP); Keisuke Okita, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 130 days.

(21) Appl. No.: 14/402,310

(22) PCT Filed: May 23, 2013

(86) PCT No.: PCT/JP2013/064409
§ 371 (c)(1),
(2) Date: Nov. 19, 2014

(87) PCT Pub. No.: WO2013/176233
PCT Pub. Date: Nov. 28, 2013

(65) Prior Publication Data
US 2015/0175973 A1    Jun. 25, 2015

Related U.S. Application Data

(60) Provisional application No. 61/650,694, filed on May 23, 2012.

(51) Int. Cl.
*C12N 5/074*     (2010.01)
*C12N 15/113*    (2010.01)
*C07K 14/005*    (2006.01)

(52) U.S. Cl.
CPC .......... *C12N 5/0696* (2013.01); *C07K 14/005* (2013.01); *C12N 15/113* (2013.01); *C12N 15/1135* (2013.01); *C12N 2310/14* (2013.01); *C12N 2310/531* (2013.01); *C12N 2501/60* (2013.01); *C12N 2501/602* (2013.01); *C12N 2501/603* (2013.01); *C12N 2501/604* (2013.01); *C12N 2501/606* (2013.01); *C12N 2501/608* (2013.01); *C12N 2501/998* (2013.01); *C12N 2506/11* (2013.01); *C12N 2506/1307* (2013.01); *C12N 2510/00* (2013.01); *C12N 2710/00022* (2013.01)

(58) Field of Classification Search
CPC .................................................. C12N 5/0696
See application file for complete search history.

(56) References Cited

U.S. PATENT DOCUMENTS

| | | | |
|---|---|---|---|
| 8,530,238 | B2 | 9/2013 | Yamanaka et al. |
| 8,900,871 | B2 | 12/2014 | Okita et al. |
| 2009/0047263 | A1 | 2/2009 | Yamanaka et al. |
| 2009/0068742 | A1 | 3/2009 | Yamanaka |
| 2010/0003757 | A1 | 1/2010 | Mack et al. |
| 2010/0093090 | A1 | 4/2010 | Deng et al. |
| 2011/0003365 | A1 | 1/2011 | Yamanaka et al. |
| 2011/0039338 | A1 | 2/2011 | Yamanaka et al. |
| 2011/0059439 | A1* | 3/2011 | Bhaumik ........... C12N 15/1086 435/6.14 |
| 2011/0223669 | A1 | 9/2011 | Yamanaka et al. |
| 2012/0196360 | A1 | 8/2012 | Okita et al. |
| 2014/0011279 | A1 | 1/2014 | Yamanaka et al. |
| 2015/0140662 | A1 | 5/2015 | Okita et al. |
| 2015/0175973 | A1 | 6/2015 | Yamanaka et al. |

FOREIGN PATENT DOCUMENTS

| | | |
|---|---|---|
| CN | 101550406 A | 10/2009 |
| JP | 2008-528038 A | 7/2008 |
| JP | 2010-273680 A | 12/2010 |
| JP | 2011-522540 A | 8/2011 |
| WO | WO 2006/083782 A2 | 8/2006 |
| WO | WO 2007/069666 A1 | 6/2007 |
| WO | WO 2007/080591 A2 | 7/2007 |
| WO | WO 2008/118820 A2 | 10/2008 |
| WO | WO 2008/144580 A2 | 11/2008 |
| WO | WO 2009/057831 A1 | 5/2009 |
| WO | WO 2009/115295 A1 | 9/2009 |
| WO | WO 2009/157593 A1 | 12/2009 |
| WO | WO 2010/147612 A1 | 12/2010 |
| WO | WO 2011/016588 A1 | 2/2011 |
| WO | WO 2011/032166 A2 | 3/2011 |
| WO | WO 2011/102531 A1 | 8/2011 |
| WO | WO 2011/119942 A1 | 9/2011 |
| WO | WO 2012/018933 A2 | 2/2012 |
| WO | WO 2013/022022 A1 | 2/2013 |

OTHER PUBLICATIONS

Yu et al (Science May 8, 2009: vol. 324, Issue 5928, pp. 797-801).*
Brown et al. (PLoS ONE. Jun. 29, 2010; 5(6): e11373-e11373).*
Okita et al (Nature Methods. May 2011 [published online Apr. 3, 2011]; 8(5): 409-412 and Supplementary information p. 1591).*
Kawamura et al. (Nature. Aug. 27, 2009; 460: 1140-1145).*
Maekawa et al. (Nature Letter. Published online Jun. 8, 2011; 474: 225-229).*

(Continued)

*Primary Examiner* — Scott Long
(74) *Attorney, Agent, or Firm* — Leydig, Voit & Mayer, Ltd.

(57) ABSTRACT

The present invention provides a production method of iPS cell, including a step of introducing the following (1) and (2):
(1) an episomal vector containing a nuclear reprogramming factor; and
(2) an episomal vector containing EBNA-1, which is different from (1),
into a somatic cell, as well as a method for improving iPS cell establishment efficiency. The present invention also provides an agent for improving iPS cell establishment efficiency, which contains an episomal vector containing a nucleic acid encoding EBNA-1, and a kit for producing an iPS cell further containing an episomal vector containing a nucleic acid encoding a nuclear reprogramming factor.

20 Claims, 6 Drawing Sheets

Specification includes a Sequence Listing.

(56) References Cited

OTHER PUBLICATIONS

Jia et al. (Nature Methods. Mar. 2010; 7(3): 197-199 and supplemental online methods 1-2; available online Feb. 7, 2010). Year: 2010).*
Loh et al. (Cell Stem Cell. 2010; 7(1): 15-19). (Year: 2010).*
Kaneda et al. (Human Gene Therapy. Feb 10, 2000; 11: 471-479) (Year: 2000).*
Chou et al., *Cell Research*, 21: 518-529 (2011).
Mack et al., *PLoS One*, 6(11): 1-14 (Nov. 2011).
Chinese Patent Office, First Office Action in Chinese Patent Application No. 201380026797.6 (dated Jan. 15, 2016) English translation.
European Patent Office, Supplementary European Search Report in European Patent Application No. 13793513 (dated Dec. 15, 2015).
Maekawa et al., *Nature*, 474(7350): 225-229 (2011).
Singapore Patent Office, Written Opinion in Singapore Patent Application No. 11201407917P (dated May 23, 2016).
Calao et al., "Direct effects of Bmil on p53 protein stability inactivates oncoprotein stress responses in embryonal cancer precursor cells at tumor initiation," *Oncogene*, advance online publication, doi:10.1038/onc.2012.368, pp. 1-11 (Aug. 20, 2012) [retrieved from internet on Mar. 5, 2013, at http://www.nature.com/onc/journal/vaop/ncurrent/pdf/onc2012368a.pdf].
Chang et al., *Stem Cells*, 27: 1042-1049 (2009).
Dijon-Grinand et al., *Fertil. Steril.*, 92(3)(Supplement): S172 P-300 (2009).
Dorigo et al., *Journal of Virology*, 78(12): 6556-6566 (2004).
Hong et al., *Nature*, 460(7259): 1132-1135 (2009).
Invitrogen Corporation, AIMV® Medium, liquid, Gibco® Invitrogen Cell Culture Catalog No. 087-0112DK, (2003-2004).
Invitrogen Corporation, STEMPRO® MSC SFM., Gibco® Invitrogen Cell Culture Catalog No. A10332-01 Datasheet, Form No. 5018, (Apr. 2008).
Invitrogen Corporation, TrypLE™ Select, Gibco® Invitrogen Corporation Catalog No. 12563-011, Form No. 3959 (Feb. 2004).
Jin et al., *Exp. and Mol. Med.*, 42(8): 574-582 (2010).
Kahoku-Shinpo, "Improved Efficiency of Establishment of iPS Cells", Kahoku-Shinpo Newspaper, p. 11 (Feb. 11, 2009).
Kaji et al., *Nature*, 458(7329): 771-775 (2009).
Kyoto University, Center for iPS Cell Research and Application (CiRA), "Episomal Vector o Mochiita Hito iPS Saibo Juritsu Hoho," Ver. 1:1-5 (Apr. 4, 2011).
Levine et al, *Cell Death and Differentiation*, 13: 1027-1036 (2006).
Mali et al., *Stem Cells*, 26: 1998-2005 (2008).
Nakagawa et al., *Nature Biotechnology*, 26(1): 101-106 (2008).
Nakagawa et al., *Proc. Natl. Acad. Sci. USA*, 107(32): 14152-14157 (2010).

Okita et al., *Nature Methods*, 8(5): 409-412 (2011).
Okita et al., *Science*, 322: 949-953 (2008).
Ries et al., *Cell*, 103: 321-330 (Oct. 13, 2000).
Rodriguez-Piza et al., *Stem Cells*, 28: 36-44 (2010).
Ross et al., *Stem Cells Dev.*, 19(8): 1221-1229 (2009).
Rowland et al., *Nature Cell Biology*, 7(11): 1074-1082 (2005).
Soldner et al., *Cell*, 136: 964-977 (2009).
Stadtfeld et al., *Science*, 322: 945-949 (2008).
Sun et al., *Proc. Natl. Acad. Sci. USA*, 106(37): 15720-15725 (2009).
Swistowski et al., *PLoS One*, 4(7): e6233 (2009).
Takahashi et al., *Cell*, 126: 663-676 (2006).
Takahashi et al., *Cell*, 131: 861-872 (2007).
Takahashi et al., PLos ONE, 4(12): e8067 (2009).
Unger et al., *Human Reprod.*, 24(10): 2567-2581 (2009).
Woltjen et al., *Nature*, 458(7239): 766-770 (2009).
Yu et al., *Science*, 318: 1917-1920 (2007).
Yu et al., *Science*, 324: 797-801 (2009).
Zhao et al., *Cell Stem Cell*, 3(5): 475-479 (2008).
Chinese Patent Office, First Office Action in Chinese Patent Application No. 201080035155.9 (dated Dec. 13, 2012).
Japanese Patent Office, Office Action in Japanese Patent Application No. 2012-523493 (dated Apr. 2, 2013).
Japanese Patent Office, International Search Report in International Patent Application No. PCT/JP2010/063733 (dated Oct. 26, 2010).
Japanese Patent Office, International Search Report in International Patent Application No. PCT/JP2013/064409 (dated Jul. 9, 2013).
U.S. Appl. No. 12/672,042, filed Apr. 1, 2010.
U.S. Appl. No. 12/672,222, filed Apr. 1, 2010.
U.S. Appl. No. 13/389,359, filed Aug. 6, 2010.
U.S. Appl. No. 13/942,208, filed Jul. 15, 2013.
U.S. Appl. No. 14/533,080, filed Nov. 4, 2014.
Blelloch et al., *Cell Stem Cell*, 1(3): 245-247 (2007).
Duinsbergen et al., *Experimental Cell Research*, 314(17): 3255-3263 (2008).
Eminli et al., *Stem Cells*, 26(10): 2467-2474 (2008).
Feng et al., *Cell Stem Cell*, 4(4): 301-312 (2009).
Kanai-Azuma et al., *Development*, 129(10): 2367-2379 (2002).
Lee et al., *Molecular and Cellular Biology*, 24(19): 8428-8436 (2004).
Maherali et al., *Cell Stem Cell*, 1(1): 55-70 (2007).
Wikipedia, "Krueppel-like factor 1," pp. 1-4 (2014) [http://en.wikipedia.org/wiki/KLF1].
Wikipedia, "Krueppel-like factor 2," pp. 1-8 (2014) [http://en.wikipedia.org/wiki/KLF2].
European Patent Office, Communication pursuant to Article 94(3) EPC in European Patent Application No. 13793513.6 (dated Nov. 4, 2016).

* cited by examiner

HIGHLY EFFICIENT METHOD FOR ESTABLISHING INDUCED PLURIPOTENT STEM CELL

CROSS-REFERENCE TO RELATED APPLICATIONS

This patent application is the U.S. national phase of International Patent Application No. PCT/JP2013/064409, filed May 23, 2013, which claims the benefit of U.S. Provisional Patent Application No. 61/650,694, filed on May 23, 2012, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 508 bytes ASCII (Text) file named "719164SequenceListing.txt," created Nov. 19, 2014.

TECHNICAL FIELD

The present invention relates to a method of efficiently establishing an induced pluripotent stem (hereinafter to be referred to as iPS) cell and an agent therefor, and the like. More particularly, the present invention relates to a production method of an iPS cell, comprising a step of introducing, into a somatic cell, (1) an episomal vector containing a nucleic acid encoding a nuclear reprogramming factor; and (2) an episomal vector containing a nucleic acid encoding EBNA-1, which is different from (1) and further, when desired, an episomal vector containing a nucleic acid encoding an inhibitor of p53 function. The present invention also relates to an agent for improving iPS cell establishment efficiency, which comprises an episomal vector containing a nucleic acid encoding EBNA-1, and the like.

BACKGROUND ART

In recent years, mouse and human iPS cells have been established one after another. Yamanaka et al. induced iPS cells by transferring the Oct3/4, Sox2, Klf4 and c-Myc genes into fibroblasts from mouse and human (patent document 1 and non-patent documents 1 and 2). On the other hand, Thomson et al. group produced human iPS cells using Nanog and Lin28 in place of Klf4 and c-Myc (patent document 2 and non-patent document 3).

Various attempts have been made to enhance the iPS cell establishment efficiency. One of them is optimization of the combination of reprogramming factors. The present inventors reported that the efficiency of iPS cell establishment can be remarkably improved by using a combination of 5 factors of Oct3/4, Sox2, Klf4, L-Myc and Lin28 as reprogramming factors, and knocking down the expression of p53 by an RNAi technique (patent document 3 and non-patent document 4). Some consider that it is desirable to avoid suppression of cancer suppressor gene p53, even if transient, particularly in consideration of the application of human iPS cells to regenerative medicine, since tumorization risk should be minimized. On the other hand, Maekawa et al. reported that the efficiency of iPS cell establishment can be more remarkably improved by introducing Glis1 together with Oct3/4, Sox2 and Klf4 (OSK), into a somatic cell than by the use of 3 factors of OSK (patent document 4 and non-patent document 5). Furthermore, Maekawa et al. reported that human iPS cell is established with about 2-fold efficiency by the use of 6 factors of Oct3/4, Sox2, Klf4, L-Myc, Lin28 and Glis1 (OSKULG) than the combination of p53 shRNA with 5 factors of Oct3/4, Sox2, Klf4, L-Myc and Lin28 (OSKUL) (U.S. provisional patent application No. 61/521,153).

Viral vectors of retrovirus, lentivirus and the like have high transgene efficiency compared to nonviral vectors, and therefore, are superior vectors since they can produce iPS cell easily. However, since retrovirus and lentivirus are incorporated into the chromosome, they have safety problems in consideration of the clinical application of iPS cell. While iPS cells free of incorporation into the chromosome by using nonviral vectors such as adenovirus vector, plasmid and the like have been reported (non-patent documents 6-8), the establishment efficiency is low when compared to retrovirus and lentivirus. In addition, a stable expression strain incorporating the reprogramming factor into the chromosome is obtained at a certain frequency even when an episomal vector generally considered to resist incorporation is used, which may be due to the requested sustained high expression of reprogramming factors under selection of iPS cells (non-patent documents 7 and 9).

On the other hand, a method using an episomal vector stably and autonomously replicable outside the chromosome shows low efficiency of the above-mentioned iPS cell establishment, low frequency of spontaneous disappearance of vector due to the discontinuation of drug selection, and requires a long time (non-patent document 8). Therefore, a method of removing a vector efficiently in a short time is desired along with the improvement of iPS cell establishment efficiency. In this connection, the present inventors found an early-self-disappearing vector that falls off rapidly from the cell and already reported the vector (patent document 3, non-patent document 4 and U.S. provisional patent application No. 61/521,153).

However, a method using an episomal vector is associated with a problem of extremely low iPS cell establishment efficiency from a particular cell, for example, blood cell, as compared to a method using other vector. Since blood cell is one of the somatic cell sources extremely useful for the construction of iPS cell bank, an episomal vector method capable of establishing iPS cell efficiently, irrespective of the kind of cells, has been desired.

DOCUMENT LIST

Patent Documents patent document 1: WO 2007/069666
patent document 2: WO 2008/118820
patent document 3: WO 2011/016588
patent document 4: WO 2011/102531

Non-Patent Documents non-patent document 1: Takahashi, K. and Yamanaka, S., Cell, 126: 663-676 (2006)
non-patent document 2: Takahashi, K. et al., Cell, 131: 861-872 (2007)
non-patent document 3: Yu, J. et al., Science, 318: 1917-1920 (2007)
non-patent document 4: Okita, K. et al., Nature Methods, 8(5), 409-412 (2011)
non-patent document 5: Maekawa, M. et al., Nature, 474: 225-229 (2011)

non-patent document 6: Stadtfeld, M. et al., Science, 322: 945-949 (2008)

non-patent document 7: Okita, K. et al., Science, 322: 949-953 (2008)

non-patent document 8: Yu, J. et al., Science, 324: 797-801 (2009)

non-patent document 9: Kaji, K. et al., Nature, 458: 771-775 (2009)

SUMMARY OF THE INVENTION

Problems to be Solved by the Invention

In view of the aforementioned situation, the present invention aims to efficiently establish a safe human iPS cell suitable for clinical application. Therefore, the first problem of the present invention is to provide a means of improving the efficiency of establishment of iPS cells, particularly human iPS cells, and a method of efficiently producing iPS cells using the means. The second problem of the present invention is to provide a method of efficiently establishing iPS cells from blood cells, which enables noninvasive obtainment of a somatic cell source toward application to regenerative medicine.

Means of Solving the Problems

The present inventors have conducted intensive studies in an attempt to solve the aforementioned problems and found for the first time that the iPS cell establishment efficiency can be strikingly increased by using, in an iPS cell establishing step, an episomal vector containing a nucleic acid encoding a nuclear reprogramming factor, together with an episomal vector containing a nucleic acid encoding EBNA-1 (hereinafter to be also referred to as "Extra EBNA-1 vector"), which is different from the above vector. In addition, the present inventors have found for the first time that iPS cell can be efficiently established from blood cells by using said method, although it was extremely difficult for conventional methods. The present invention has been completed based on such findings.

Accordingly, the present invention encompasses the following.

[1] A method of producing an iPS cell, comprising a step of introducing the following (1) and (2):
(1) one or more episomal vectors containing a nucleic acid encoding a nuclear reprogramming factor; and
(2) an episomal vector containing a nucleic acid encoding EBNA-1, which is different from (1) into a somatic cell.
[2] The method of [1], further comprising introducing a nucleic acid, encoding an inhibitor of p53 function, in the form of an episomal vector.
[3] The method of [2], wherein the aforementioned inhibitor of p53 function is p53 shRNA or a dominant negative mutant of p53.
[4] The method of [3], wherein the aforementioned dominant negative mutant of p53 is p53DD.
[5] The method of any of [1]-[4], wherein the aforementioned nuclear reprogramming factor is one or more selected from the group consisting of the members of Oct family, Klf family, Sox family, Myc family, Lin family and Glis family.
[6] The method of [5], wherein the aforementioned nuclear reprogramming factors are Oct3/4, Klf4, Sox2, L-Myc and Lin28.
[7] The method of [6], wherein the aforementioned nuclear reprogramming factors are Oct3/4, Klf4, Sox2, L-Myc, Lin28 and Glis1.
[8] The method of any of [1]-[7], wherein the aforementioned nucleic acid encoding a nuclear reprogramming factor is divided and contained in 2 or 3 episomal vectors.
[9] The method of [1], wherein the aforementioned episomal vectors containing the nucleic acid encoding a nuclear reprogramming factor are pCEB-hSK-O and pCEB-hUL-G.
[10] The method of [1], wherein the aforementioned episomal vectors containing the nucleic acid encoding a nuclear reprogramming factor are pCXLE-hOCT3/4, pCXLE-hSK and pCXLE-hUL.
[11] The method of [2], wherein the aforementioned episomal vectors containing the nucleic acid encoding a nuclear reprogramming factor are pCXLE-hOCT3/4-shp53-F, pCXLE-hSK and pCXLE-hUL.
[12] The method of [2], wherein the aforementioned episomal vectors containing the nucleic acid encoding a nuclear reprogramming factor are pCE-hOCT3/4-shp53, pCE-hSK and pCE-hUL.
[13] The method of [2], wherein the aforementioned episomal plasmid vectors containing the nucleic acid encoding a nuclear reprogramming factor are pCE-hOCT3/4, pCE-hSK and pCE-hUL, and the aforementioned episomal vector containing the nucleic acid encoding an inhibitor of p53 function is pCE-mp53DD.
[14] The method of any of [9]-[11], wherein the aforementioned plasmid vector containing the nucleic acid encoding EBNA-1 is pCXWB-EBNA1.
[15] The method of [12] or [13], wherein the aforementioned plasmid vector containing the nucleic acid encoding EBNA-1 is pCXB-EBNA1.
[16] The method of any of [1]-[15], wherein the aforementioned somatic cell is selected from human fibroblast (HDF) and blood cell.
[17] The method of [16], wherein the aforementioned blood cell is a peripheral blood mononuclear cell (PMNC).
[18] The method of [17], wherein the aforementioned peripheral blood mononuclear cell (PMNC) is a T cell.
[19] A method of improving iPS cell establishment efficiency, comprising a step of introducing, into a somatic cell, one or more episomal vectors containing a nucleic acid encoding a nuclear reprogramming factor, wherein a different episomal vector containing a nucleic acid encoding EBNA-1 is introduced into the somatic cell together with the vector.
[20] The method of [19], further comprising introducing a nucleic acid, encoding an inhibitor of p53 function, in the form of an episomal vector.
[21] The method of [20], wherein the aforementioned inhibitor of p53 function is p53 shRNA or a dominant-negative mutant of p53.
[22] The method of [21], wherein the aforementioned dominant-negative mutant of p53 is p53DD.
[23] An agent for improving iPS cell establishment efficiency, comprising an episomal vector containing a nucleic acid encoding EBNA-1.
[24] A kit for producing an iPS cell, comprising the following (1) and (2):
(1) an episomal vector containing a nucleic acid encoding a nuclear reprogramming factor; and
(2) an episomal vector containing a nucleic acid encoding EBNA-1, which is different from (1).

[25] The kit of [24], further comprising a nucleic acid encoding an inhibitor of p53 function A, in the form of an episomal vector.

[26] The kit of [25], wherein the aforementioned inhibitor of p53 function is p53 shRNA or a dominant-negative mutant of p53.

[27] The kit of [26], wherein the aforementioned dominant-negative mutant of p53 is p53DD.

[28] The kit of [24], wherein the aforementioned episomal vectors containing the nucleic acid encoding a nuclear reprogramming factor are pCEB-hSK-O and pCEB-hUL-G.

[29] The kit of [24], wherein the aforementioned episomal vectors containing the nucleic acid encoding a nuclear reprogramming factor are pCXLE-hOCT3/4, pCXLE-hSK and pCXLE-hUL.

[30] The kit of [25], wherein the aforementioned episomal vectors containing the nucleic acid encoding a nuclear reprogramming factor are pCXLE-hOCT3/4-shp53-F, pCXLE-hSK and pCXLE-hUL.

[31] The kit of [25], wherein the aforementioned episomal vectors containing the nucleic acid encoding a nuclear reprogramming factor are pCE-hOCT3/4-shp53, pCE-hSK and pCE-hUL.

[32] The kit of [25], wherein the aforementioned episomal plasmid vectors containing the nucleic acid encoding a nuclear reprogramming factor are pCE-hOCT3/4, pCE-hSK and pCE-hUL, and the aforementioned episomal vector containing the nucleic acid encoding an inhibitor of p53 function is pCE-mp53DD.

[33] The kit of any of [28]-[30], wherein the aforementioned plasmid vector containing the nucleic acid encoding EBNA-1 is pCXWB-EBNA1.

[34] The kit of [31] or [32], wherein the aforementioned plasmid vector containing the nucleic acid encoding EBNA-1 is pCXB-EBNA1.

[35] A method of producing a somatic cell, comprising subjecting an iPS cell obtained by the method of any of [1]-[18] to a differentiation treatment to allow for differentiation into a somatic cell.

Effect of the Invention

Use of Extra EBNA-1 vector in the nuclear reprogramming step of somatic cell strikingly increases the establishment efficiency of iPS cell, and enables more efficient provision of human iPS cell. Moreover, use of Extra EBNA-1 vector enables efficient establishment of iPS cell from blood cell, which is extremely difficult by conventional methods, which in turn enables obtainment of a somatic cell source in a noninvasive form. Therefore, the present invention is extremely useful for the application of human iPS cell to regenerative medicine.

DESCRIPTION OF EMBODIMENTS

[Detailed Description of the Invention]

Figure 1:
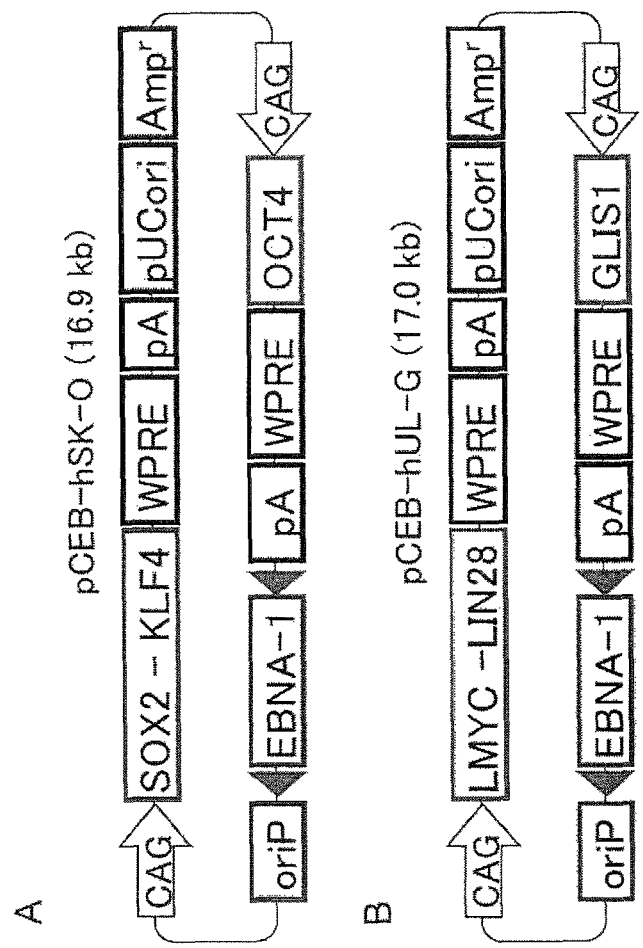
FIG. 1A shows the structure of pCEB-hSK-O.
FIG. 1B shows the structure of pCEB-hUL-G.

The present invention provides a production method of iPS cell, comprising a step of introducing, into a somatic cell, (1) one or more episomal vectors containing a nucleic acid encoding a nuclear reprogramming factor; and (2) an episomal vector containing EBNA-1, which is different from (1) and further, when desired, an episomal vector containing a nucleic acid encoding an inhibitor of p53 function (in the episomal vector, the nucleic acid encoding an inhibitor of p53 function may be contained singly, or contained together with a nucleic acid encoding a nuclear reprogramming factor, in any of the episomal vectors of the aforementioned (1)). The present invention also provides an agent for improving iPS cell establishment efficiency, which comprises an episomal vector containing a nucleic acid encoding EBNA-1, and the like.

(A) Sources of Somatic Cells

Any cells other than germ cells of mammalian origin (e.g., humans, mice, monkeys, pigs, rats etc.) can be used as starting material for the production of iPS cells. Examples include keratinizing epithelial cells (e.g., keratinized epidermal cells), mucosal epithelial cells (e.g., epithelial cells of the superficial layer of tongue), exocrine gland epithelial cells (e.g., mammary gland cells), hormone-secreting cells (e.g., adrenomedullary cells), cells for metabolism or storage (e.g., liver cells), intimal epithelial cells constituting interfaces (e.g., type I alveolar cells), intimal epithelial cells of the obturator canal (e.g., vascular endothelial cells), cells having cilia with transporting capability (e.g., airway epithelial cells), cells for extracellular matrix secretion (e.g., fibroblasts), constrictive cells (e.g., smooth muscle cells), cells of the blood and the immune system (e.g., T lymphocytes), sense-related cells (e.g., bacillary cells), autonomic nervous system neurons (e.g., cholinergic neurons), sustentacular cells of sensory organs and peripheral neurons (e.g., satellite cells), nerve cells and glia cells of the central nervous system (e.g., astroglia cells), pigment cells (e.g., retinal pigment epithelial cells), progenitor cells (tissue progenitor cells) thereof and the like. There is no limitation on the degree of cell differentiation, the age of an animal from which cells are collected and the like; even undifferentiated progenitor cells (including somatic stem cells) and finally differentiated mature cells can be used alike as sources of somatic cells in the present invention. Examples of undifferentiated progenitor cells include tissue stem cells (somatic stem cells) such as neural stem cells, hematopoietic stem cells, mesenchymal stem cells, and dental pulp stem cells. Particularly, since blood cells (peripheral blood mononuclear cell (including T cell and non-T cell (including CD34 positive cell and progenitor stem cell)), peripheral blood lymphocyte, cord blood cell and the like) are easily available and do not accompany invasion, utilization thereof as a somatic cell source for the iPS cell bank is expected. Also, since pulp stem cells can be prepared by isolation from a wisdom tooth, a tooth pulled out due to a periodontal disease and the like, they are easily available and utilization thereof as a somatic cell source for the iPS cell bank is expected.

When a peripheral blood mononuclear cell is used as the somatic cell, T cell receptor (TCR) gene locus may or may not contain V(D)J recombination. A preferable example of the peripheral blood mononuclear cell include, but is not limited to, T cell wherein T cell receptor (TCR) gene locus contains V(D)J recombination.

The choice of mammal individual as a source of somatic cells is not particularly limited; however, when the iPS cells obtained are to be used for regenerative medicine in humans, it is preferable, from the viewpoint of prevention of graft rejection, to collect the somatic cells from a patient or another person with the same or substantially the same HLA type as that of the patient. "Substantially the same HLA type" as used herein means that the HLA type of donor matches with that of patient to the extent that the transplanted cells, which have been obtained by inducing differentiation of iPS cells derived from the donor's somatic cells, can be engrafted when they are transplanted to the patient with use of immunosuppressant and the like. For example, it includes an HLA type wherein major HLAs (e.g., the three major loci of HLA-A, HLA-B and HLA-DR, the four loci further including HLA-Cw) are identical (hereinafter the same meaning shall apply) and the like. When the iPS cells obtained are not to be administered (transplanted) to a human, but used as, for example, a source of cells for screening for evaluating a patient's drug susceptibility or adverse reactions, it is likewise desired to collect the somatic cells from the patient or another person with the same genetic polymorphism correlating with the drug susceptibility or adverse reactions.

When a mammalian individual as a source of somatic cells is a human, his/her age is generally 20's-60's, preferably, 20's-40's, though not limited thereto.

Somatic cells isolated from a mammal can be pre-cultured using a medium known per se suitable for their cultivation according to the choice of cells before being subjected to the nuclear reprogramming step. Examples of such media include, but are not limited to, minimal essential medium (MEM) containing about 5 to 20% fetal bovine serum (FCS), Dulbecco's modified Eagle medium (DMEM), RPMI1640 medium, 199 medium, F12 medium, and the like. For example, when a pulp stem cell is used as a somatic cell, a medium for mesenchymal stem cells such as Mesenchymal stem cells basal medium (Lonza) and the like are preferably used. When blood cells are used, IL-2, anti-CD3 antibody and anti-CD28 antibody may be added to the culture medium since T cells are used on concentration. Similarly, IL-3, IL-6, G-CSF and GM-CSF may be added to the culture medium since non-T cells are used on concentration. The cells may be concentrated before or after introduction the episomal vectors of the present invention of the above-mentioned (1) and (2) (sometimes additional episomal vector containing a nucleic acid encoding an inhibitor of p53 function; hereinafter to be also referred to as "the vector set of the present invention"). When the vector set of the present invention and, for example, a transfer reagent such as cationic liposome for bringing the somatic cell into contact with iPS cell establishment efficiency improver, if required, are used, it is sometimes preferable that the medium have been replaced with a serum-free medium so as to prevent the transfer efficiency from decreasing.

To obtain a completely xeno-free human iPS cell suitable for human clinical application, a medium free of a component derived from a non-human animal such as FCS and the like is more desirable. A medium obtained by adding various human-derived components suitable for the culture of somatic cell (particularly, recombinant human protein such as growth factor and the like), non-essential amino acids, vitamins and the like to a basic medium is commercially available, and those of ordinary skill in the art can select an appropriate xeno-free medium for a somatic cell source. Somatic cell precultured in a xeno-free medium is detached from a culture container by using a suitable xeno-free cell detachment solution, recovered and brought into contact with the vector set of the present invention.

(B) Nuclear Reprogramming Factor (Also Simply Referred to as "Reprogramming Factor")

The "nuclear reprogramming factor" in the present invention means a proteinaceous factor (group) capable of inducing iPS cell from somatic cell. The nuclear reprogramming factor to be used in the present invention may be any proteinaceous factor (group) as long as it can induce iPS cell by introducing a nucleic acid encoding same into the somatic cell. For example, it may be one or more proteinaceous factors selected from the group consisting of the members of Oct family, Klf family, Sox family, Myc family, Lin family and Glis family. Preferably, the nuclear reprogramming factor to be used in the present invention contains at least Oct3/4, Klf4 and Sox2 (Klf4 and/or Sox2 may be replaced with other factor(s) reported to be able to replace the functions thereof) and, when an inhibitor of p53 function is not used in combination, L-Myc and Lin28 or Lin28b are preferably further combined as nuclear reprogramming factors. The nuclear reprogramming factor to be used in the present invention is characteristically free of Nanog. Specifically, the following combinations can be recited as the nuclear reprogramming factor.

(1) Oct3/4, Klf4, Sox2, L-Myc (here, Sox2 is replaceable with Sox1, Sox3, Sox15, Sox17 or Sox18; Klf4 is replaceable with Klf1, Klf2 or Klf5)
(2) Oct3/4, Klf4, Sox2, L-Myc, TERT, SV40 Large T antigen (hereinafter SV40LT)
(3) Oct3/4, Klf4, Sox2, L-Myc, TERT, HPV16 E6
(4) Oct3/4, Klf4, Sox2, L-Myc, TERT, HPV16 E7
(5) Oct3/4, Klf4, Sox2, L-Myc, TERT, HPV16 E6, HPV16 E7
(6) Oct3/4, Klf4, Sox2, L-Myc, TERT, Bmi1
(7) Oct3/4, Klf4, Sox2, L-Myc, Lin28
(8) Oct3/4, Klf4, Sox2, L-Myc, Lin28, Glis1
(9) Oct3/4, Klf4, Sox2, L-Myc, Lin28, SV40LT

(10) Oct3/4, Klf4, Sox2, L-Myc, Lin28, TERT, SV40LT
(11) Oct3/4, Klf4, Sox2, L-Myc, SV40LT
(12) Oct3/4, Esrrb, Sox2, L-Myc (Esrrb is replaceable with Esrrg)
(13) Oct3/4, Klf4, Sox2
(14) Oct3/4, Klf4, Sox2, TERT, SV40LT
(15) Oct3/4, Klf4, Sox2, TERT, HPV16 E6
(16) Oct3/4, Klf4, Sox2, TERT, HPV16 E7
(17) Oct3/4, Klf4, Sox2, TERT, HPV16 E6, HPV16 E7
(18) Oct3/4, Klf4, Sox2, TERT, Bmi1
(19) Oct3/4, Klf4, Sox2, Lin28
(20) Oct3/4, Klf4, Sox2, Lin28, SV40LT
(21) Oct3/4, Klf4, Sox2, Lin28, TERT, SV40LT
(22) Oct3/4, Klf4, Sox2, SV40LT
(23) Oct3/4, Esrrb, Sox2 (Esrrb is replaceable with Esrrg)

In the above, Lin28b can also be used instead of Lin28. When Esrrb or Esrrg is used (the above-mentioned (12) and (23)), Klf4 may be used in combination.

Any combination that does not fall in (1) to (23) above but comprises all the constituents of any one of (1) to (22) and further comprises an optionally chosen other substance can also be included in the scope of "nuclear reprogramming factors" in the present invention. Provided that the somatic cell to undergo nuclear reprogramming is endogenously expressing one or more of the constituents of any one of (1) to (23) above at a level sufficient to cause nuclear reprogramming, a combination of only the remaining constituents excluding the one or more constituents can also be included in the scope of "nuclear reprogramming factors" in the present invention.

Among these combinations, 5 factors of Oct3/4 (sometimes to be abbreviated as "O"), Sox2 (sometimes to be abbreviated as "S"), Klf4 (sometimes to be abbreviated as "K"), Lin28 (sometimes to be abbreviated as "L") and L-Myc (sometimes to be abbreviated as "U"), and 6 factors of Oct3/4, Sox2, Klf4, Lin28, L-Myc and Glis1 (sometimes to be abbreviated as "G") are preferable examples.

Information on the mouse and human cDNA sequences of the aforementioned nuclear reprogramming factors is available with reference to the NCBI accession numbers mentioned in WO 2007/069666 (in the publication, Nanog is described as ECAT4. Mouse and human cDNA sequence information on Lin28, Lin28b, Esrrb, Esrrg, L-Myc and Glis1 can be acquired by referring to the following NCBI accession numbers, respectively); those skilled in the art are easily able to isolate these cDNAs.

| Name of gene | Mouse | Human |
| --- | --- | --- |
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |
| L-Myc | NM_008506 | NM_001033081 |
| Glis1 | NM_147221 | NM_147193 |

(c) Inhibitors of p38 Function

In the present invention, it is more preferable to contact an inhibitor of p53 function with a somatic cell, in addition to the above-mentioned nuclear reprogramming factor. As mentioned herein, "an inhibitor of p53 function" may be any substance, as far as it is capable of inhibiting either (a) the function of the p53 protein or (b) the expression of the p53 gene. That is, not only substances that act directly on the p53 protein to inhibit the function thereof and substances that act directly on the p53 gene to inhibit the expression thereof, but also substances that act on a factor involved in p53 signal transduction to result in inhibition of the function of the p53 protein or the expression of the p53 gene, are also included in the scope of "an inhibitor of p53 function" as mentioned herein.

Examples of the substances that inhibit the function of the p53 protein include, but are not limited to, a chemical inhibitor of p53, a dominant-negative mutant of p53, an anti-p53 antagonist antibody, a decoy nucleic acid containing a consensus sequence of p53 response element, a p53 pathway inhibiter and the like. Preferred are a chemical inhibitory substance of p53, a dominant-negative mutant of p53 and a p53 pathway inhibitory substance, and more preferred is a dominant-negative mutant of p53. On the other hand, as a preferable substance that inhibits the expression of p53 gene, siRNA and shRNA to p53 can be mentioned.

Specific examples of the inhibitor of p53 function, a method of obtaining them and a method of contacting them with somatic cell are detailedly described in WO 2009/157593.

In a preferable embodiment of the present invention, p53 shRNA or dominant-negative mutant of p53 as an inhibitor of p53 function is introduced, in the form of an episomal vector containing a nucleic acid encoding same, into a somatic cell to achieve contact with the somatic cell.

A particularly preferable dominant-negative mutant of p53 in the present invention is p53DD wherein the 14-301st (corresponding to the 11-304th in human p53) amino acids of mouse p53 have been deleted (Bowman, T., Genes Develop., 10, 826-835 (1996)).

A nucleic acid encoding the dominant-negative mutant of p53 can be obtained, for example, by the following method. First, a suitable oligonucleotide is synthesized as a probe or primer based on the mouse or human p53 cDNA sequence information, and a mouse or human p53 cDNA is cloned from a mRNA, cDNA or cDNA library derived from a mouse or human cell or tissue, using the hybridization method or the (RT-)PCR method, and is subcloned into an appropriate plasmid. In the case of a deletion variant such as p53DD, a primer is designed on the outside of the site to be deleted, using which inverse PCR is performed using a plasmid inserted with p53 cDNA as a template, whereby a cDNA encoding the object dominant-negative mutant is obtained.

The isolated cDNA is inserted into the below-mentioned episomal vector in the same manner as in the aforementioned nucleic acid encoding a nuclear reprogramming factor, and can be introduced into the somatic cell.

An siRNA against p53 can be designed on the basis of the mouse or human p53 cDNA sequence information, in accordance with, for example, the rules proposed by Elbashir et al. (*Genes Dev.*, 15, 188-200 (2001)). The target sequence candidates selected on the basis of the above-described rules are examined for homology to sequences of 16-17 bases in succession in mRNAs other than the target, using a homology search software program such as BLAST (http://www.ncbi.nlm.nih.gov/BLAST/), so as to confirm the specificity of the target sequences selected. For the target sequences for which the specificity has been confirmed, a double strand RNA consisting of a sense strand of 19-21 bases and an antisense strand complementary thereto is linked via any linker sequence capable of forming a loop structure (e.g., about 8-25 bases), whereby siRNA can be designed.

To be specific, shRNA to human p53, having sequence 5'-GACTCCAGTGGTAATCTACTGctcgagCAGTAGATTA-CCACTGGAGTC-3' (SEQ ID NO: 1; underlined part is the target sequence of p53, capital letters show the part forming dsRNA) and the like can be used as particularly preferable shRNA in the present invention.

For a vector expressing a DNA encoding shRNA, while a pol II promoter (e.g., immediate-early promoter of CMV) may be used as the promoter, it is a common practice to use a pol III promoter in order to allow the accurate transcription of short RNA. As the pol III promoter, mouse and human U6-snRNA promoters, human H1-RNase P RNA promoter, human valine-tRNA promoter and the like can be mentioned. As a transcription termination signal, a sequence of 4 or more T residues in succession is used.

The shRNA expression cassette thus constructed is inserted into the below-mentioned episomal vector in the same manner as with the aforementioned nucleic acid encoding a nuclear reprogramming factor, and can be introduced into a somatic cell.

(D) Expression Cassette

The above-mentioned nucleic acid encoding a nuclear reprogramming factor (and a nucleic acid encoding an inhibitor of p53 function) can constitute the expression cassette singly or in any combination, and these expression cassettes can be contained in any combination in an episomal vector. For example, when Oct3/4, Sox2, Klf4, Lin28 and L-Myc are used as reprogramming factors, five nucleic acids encoding these reprogramming factors are contained as the following 3 expression cassettes in an episomal vector.

(a) an expression cassette containing nucleic acid (O) encoding Oct3/4;
(b) an expression cassette wherein nucleic acid (S) encoding Sox2 and nucleic acid (K) encoding Klf4 are linked in this order (S-K) in the 5' to 3' orientation via an interlying sequence enabling dicistronic expression; and
(c) an expression cassette wherein nucleic acid (U) encoding L-Myc and nucleic acid (L) encoding Lin28 are linked in this order (U-L) in the 5' to 3' orientation via an interlying sequence enabling dicistronic expression In a preferable embodiment of the present invention, Glis1 is further used as a reprogramming factor in addition to the above-mentioned 5 reprogramming factors. In this case, a nucleic acid encoding 6 reprogramming factors is contained as 4 expression cassettes of the above-mentioned 3 expression cassettes (a)-(c), and
(d) an expression cassette containing nucleic acid (G) encoding Glis1
in an episomal vector.

In another embodiment, 5 reprogramming factors of Oct3/4, Sox2, Klf4, Lin28 and L-Myc are combined with p53 shRNA or p53DD. In this case, six nucleic acids encoding 5 reprogramming factors and p53 shRNA or p53DD are contained as the following 4 expression cassettes in an episomal vector.

(a) an expression cassette containing nucleic acid (O) encoding Oct3/4;
(b) an expression cassette wherein nucleic acid (S) encoding Sox2 and nucleic acid (K) encoding Klf4 are linked in this order (S-K) in the 5' to 3' orientation via an interlying sequence enabling dicistronic expression;
(c) an expression cassette wherein nucleic acid (U) encoding L-Myc and nucleic acid (L) encoding Lin28 are linked in this order (U-L) in the 5' to 3' orientation via an interlying sequence enabling dicistronic expression; and
(d') an expression cassette containing a nucleic acid encoding p53 shRNA or (d") an expression cassette containing a nucleic acid encoding p53DD As the "interlying sequence enabling dicistronic expression", 2A sequence of foot-and-mouth disease virus (PLoS ONE 3, e2532, 2008, Stem Cells 25, 1707, 2007), IRES sequence (U.S. Pat. No. 4,937,190) and the like, preferably 2A sequence, can be used. The "expression cassette" contains a reprogramming factor and/or a nucleic acid encoding an inhibitor of p53 function (O, S-K, U-L, G and the like), as well as at least a promoter operably linked to the nucleic acid. Examples of the promoter for a reprogramming factor or a nucleic acid encoding a dominant-negative mutant of p53 include the EF1α promoter, the CAG promoter, the SRα promoter, the SV40 promoter, the LTR promoter, the CMV (cytomegalovirus) promoter, the RSV (Rous sarcoma virus) promoter, the MoMuLV (Moloney mouse leukemia virus) LTR, the HSV-TK (herpes simplex virus thymidine kinase) promoter and the like, with preference given to the EF1α promoter, the CAG promoter, the MoMuLV LTR, the CMV promoter, the SRα promoter and the like. Furthermore, the expression cassette may contain, in addition to the basal promoter sequence, an enhancer sequence for potentiating the expression of the reprogramming factor (e.g., CMV early-immediate enhancer etc.). In the case of a nucleic acid encoding p53 shRNA, pol III promoter such as U6 promoter and the like is preferably used as a promoter as mentioned above.

Preferably, the expression cassette of the present invention contains, in addition to the promoter, a polyA addition signal at the 3' downstream of the nucleic acid encoding a reprogramming factor or dominant-negative mutant of p53. In the case of a nucleic acid encoding p53 shRNA, a sequence of 4 or more continuous T residues is preferably contained as a transcription termination signal at the 3' downstream of the nucleic acid. In the expression cassette of the present invention, moreover, woodchuck hepatitis virus posttranscriptional regulatory element (WPRE) sequence may be inserted between, for example, the coding region and polyA addition signal of the reprogramming factor and the dominant-negative mutant, in an attempt to improve the stability of the reprogramming factor and mRNA of the dominant-negative mutant of p53.

(E) Episomal Vector

Examples of the episomal vector to be used in the present invention include a vector comprising, as a vector component, a sequence derived from EBV, SV40 and the like necessary for self-replication in a mammalian cell. The vector component necessary for self-replication in a mammalian cell is specifically exemplified by a replication origin functional in mammalian cells and a gene that encodes a protein that binds to the replication origin to control the replication. Examples thereof include the replication origin oriP and the EBNA-1 gene for EBV, and the replication origin on and the SV40 large T antigen gene for SV40. More preferably, oriP and EBNA-1 gene are used.

When desired, the episomal vector may further contain replication origin of bacterium or yeast (e.g., pUC ori, ColE1 ori, 2μ on etc.), selection marker gene (e.g., ampicillin resistant gene, auxotrophic complementary gene) and the like to enable mass amplification in bacteria and yeast such as *Escherichia coli* and the like. Moreover, when desired, for example, the dihydrofolate reductase gene, the neomycin resistance gene and the like can be further contained as a selection marker gene in a mammalian cell. Furthermore, the episomal vector can contain a multicloning site to facilitate insertion of an expression cassette of a nucleic acid encoding a reprogramming factor. In one embodiment, the promoter, enhancer, polyA addition signal, WPRE sequence and the like in the above-mentioned expression cassette are previously contained on the episomal vector, and the episomal vector can also be designed to construct a transgene vector by inserting a nucleic acid encoding a reprogramming factor between the promoter and the polyA addition signal (WPRE sequence when vector contains WPRE sequence). In such case, the episomal vector preferably contains a multicloning site between the promoter and the polyA addition signal (WPRE sequence when vector contains WPRE sequence).

The vector set of the present invention can be constructed by including 1 or 2 of the above-mentioned expression cassettes (a)-(c), or (a)-(d), (d') or (d") in each of plural (preferably, 2, 3 or 4) episomal vectors. In this regard, the present inventors previously disclosed that a combination of plural expression cassettes and the order thereof on an episomal vector markedly affects the iPS cell establishment efficiency (U.S. provisional patent application No. 61/521, 153).

In the present invention, the iPS cell establishment efficiency is markedly improved by the combined use of Extra EBNA-1 vectors. Therefore, the vector set of the present invention may contain 1 or 2 of the above-mentioned expression cassettes (a)-(c), or (a)-(d), (d') or (d") on 2, 3 or 4 episomal vectors at any combination and in any order at any positions.

However, in one preferable embodiment, the vector set of the present invention is constructed by mounting two of the above-mentioned expression cassettes (a)-(d) on two episomal vectors according to the following rules (U.S. provisional patent application No. 61/521,153).

When expression cassettes are set in the 5' to 3' orientation in the order of [expression cassette A]-[expression cassette B] with the 3'-side of a gene (sense strand) encoding a protein (e.g., EBNA-1, SV40 large T antigen etc., preferably EBNA-1), which binds to the functional replication origin in a mammalian cell and regulates replication of the vector in the mammalian cell, as the origin (hereinafter the position of expression cassette on episomal vector is always shown by using this origin),
1) the expression cassette of the above-mentioned (a) (including nucleic acid (O) encoding Oct3/4) is disposed at the position of expression cassette B; preferably,
2) the expression cassette of the above-mentioned (b) wherein nucleic acid (S) encoding Sox2 and nucleic acid (K) encoding Klf4 are linked in this order (S-K) in the 5' to 3' orientation via an interlying sequence enabling dicistronic expression is disposed at the position of expression cassette A.

Here, the above-mentioned expression cassette (a) and the above-mentioned expression cassette (b) may be set on (i) the same episomal vector (disposed on the first episomal vector in the order of (b)-(a)), or set on (ii) different episomal vectors (disposed on the first episomal vector in the order of (c) or (d)-(a), and disposed on the second episomal vector in the order of (b)-(d) or (c)). The above-mentioned (i) includes two kinds of combination: (ia) a combination of the first episomal vectors: (b)-(a) (order of reprogramming factors SK-O), and the second expression vectors: (c)-(d) (order of reprogramming factors UL-G), and (ib) a combination of the first episomal vectors: (b)-(a) (order of reprogramming factors SK-O), and the second expression vectors: (d)-(c) (order of reprogramming factor G-UL). The above-mentioned (ii) includes two kinds of combination: (iia) a combination of the first episomal vectors: (c)-(a) (order of reprogramming factors UL-O) and the second expression vectors: (b)-(d) (order of reprogramming factors SK-G), and (iib) a combination of the first episomal vectors: (d)-(a) (order of reprogramming factors G-O) and the second expression vectors: (b)-(c) (order of reprogramming factors SK-UL).

Of these, a particularly preferable combination is the above-mentioned combination (ia), i.e., a combination of the first episomal vectors: (b)-(a) (order of reprogramming factors SK-O), and the second expression vectors: (c)-(d) (order of reprogramming factors UL-G). More specifically, the combination of pCEB-hSK-O and pCEB-hUL-G shown in the below-mentioned Example and FIG. 1 can be mentioned.

In the order of the above-mentioned expression cassettes, the orientation of transcription of each expression cassette is not particularly limited, and two expression cassettes may be inserted such that they are transcribed in the same orientation (head-to-tail), or inserted such that they are transcribed in the opposite orientations (head-to-head or tail-to-tail). The orientation of transcription of each expression cassette may be the same as or opposite from the orientation of transcription of a gene encoding a protein that binds to the functional replication origin in a mammalian cell and regulates replication of the vector in the mammalian cell. In one preferable embodiment, all expression cassettes are mounted on the vector such that they are transcribed in the same orientation as that of the gene.

Figure 2:
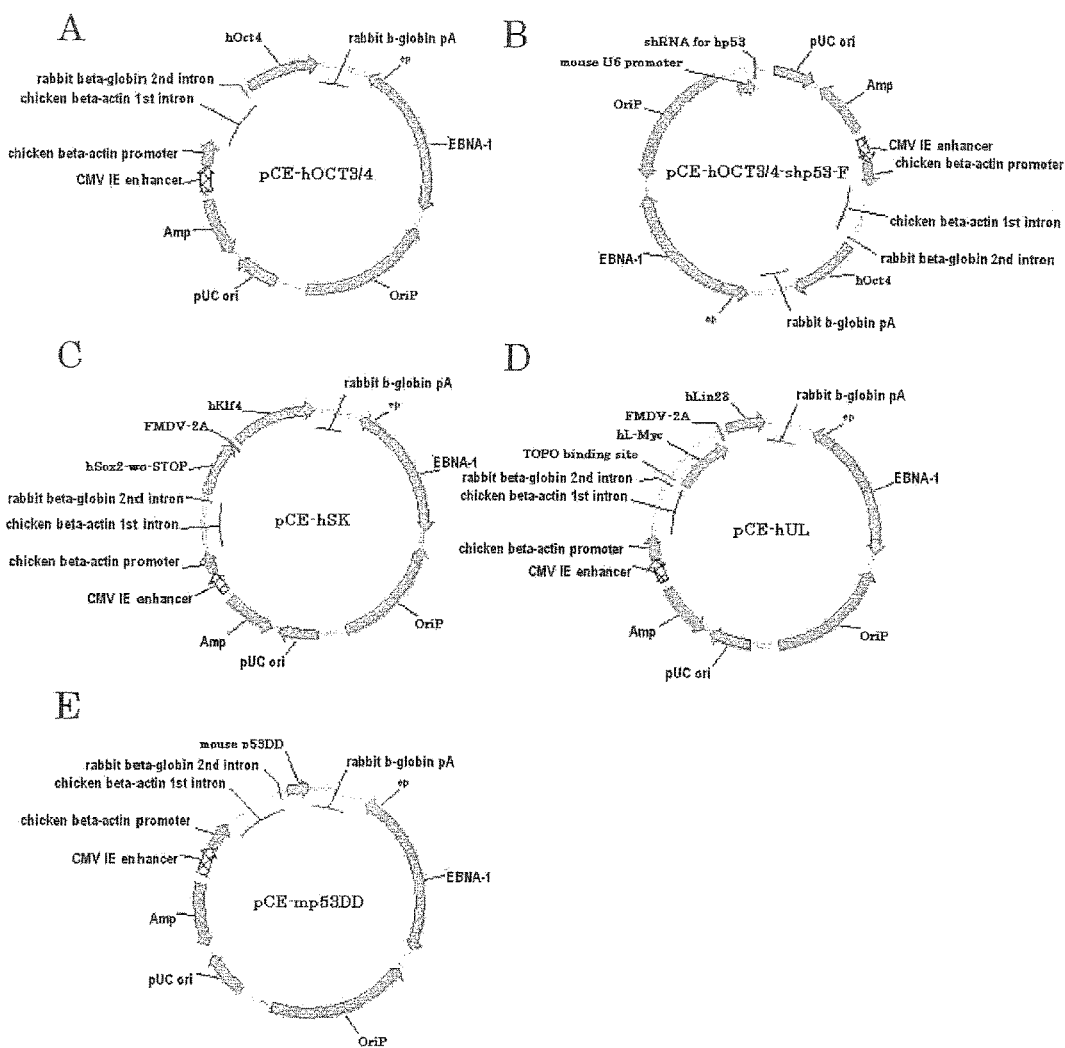
FIG. 2A-E show the structures of various episomal plasmids (pCE-hOCT3/4, pCE-hOCT3/4-shp53, pCE-hSK, pCE-hUL and pCE-mp53DD).

In another preferable embodiment, the vector set of the present invention comprises the above-mentioned expression cassettes (a)-(c) respectively mounted on 3 episomal vectors. More specifically, Examples of the 3 episomal vectors include pCXLE-hOCT3/4 (Addgene#27076), pCXLE-hSK (Addgene#27078) and pCXLE-hUL (Addgene#27080) (see Nat. Methods, 8(5): 409-412 (2011)), and pCE-hOCT3/4, pCE-hSK and pCE-hUL shown in the below-mentioned Examples and FIG. 2.

When the vector set further contains an expression cassette of an inhibitor of p53 function (i.e., expression cassette of the above-mentioned (d') or (d")), the expression cassette may be singly mounted on a separate episomal vector (total 4 episomal vectors). Specific examples include pCE-mp53DD and the like shown in the below-mentioned Examples and FIG. 2.

Alternatively, an expression cassette of the inhibitor of p53 function may be mounted together on any of the 3 episomal vectors containing the above-mentioned expression cassettes (a)-(c). Preferably, it may be, but is not limited to be, mounted on an episomal vector together with the above-mentioned expression cassette (a). When it is mounted on an episomal vector together with a nucleic acid encoding a reprogramming factor, the order thereof is not particularly limited. For example, they can be set in the order of expression cassette of inhibitor of p53 function-expression cassette of reprogramming factor. Specific examples include pCXLE-hOCT3/4-shp53-F (Addgene#27077) (also referred to as "pCXLE-hOCT3/4-shp53", see Nat. Methods, 8(5): 409-412 (2011)), and pCE-hOCT3/4-shp53-F (also referred to as "pCE-hOCT3/4-shp53") shown in the below-mentioned Examples and FIG. 2.

The episomal vector in the present invention may or may not contain a loxP sequence on the 5'-side and the 3'-side of the vector component necessary for replication of the vector in a mammalian cell. Preferably, an episomal vector having a loxP sequence on the 5'-side and the 3'-side of the vector component in the same orientation can be used. Since episomal vector is capable of autonomous replication outside the chromosome, even when it is not incorporated in the genome, stable expression in a host cell can be provided. Once the iPS cell is established, the vector is desirably removed rapidly. The autonomous replication ability of an episomal vector can be made to disappear by placing a vector component necessary for replication of an episomal vector in a mammalian cell flanked by two loxP sequences, allowing Cre recombinase to act thereon and cleaving out the vector component, and the vector can be made to fall off from the iPS cell in an early stage.

The loxP sequences useful in the present invention include, in addition to the bacteriophage P1-derived wild type loxP sequence, optionally chosen mutant loxP sequences capable of deleting the sequence flanked by the loxP sequence by recombination when placed in the same orientation at positions flanking a vector component necessary for the replication of episomal vector in a mammalian cell. Examples of such mutant loxP sequences include lox71, mutated in 5' repeat, lox66, mutated in 3' repeat, and lox2272 and lox511, mutated in spacer portion. Although the two loxP sequences placed on the 5' and 3' sides of the vector component may be identical or not, the two mutant loxP sequences mutated in spacer portion must be identical (e.g., a pair of lox2272 sequences, a pair of lox511 sequences). Preference is given to a combination of a mutant loxP sequence mutated in 5' repeat (e.g., lox71) and a mutant loxP sequence mutated in 3' repeat (e.g., lox66). In this case, the loxP sequences remaining on the chromosome have double mutations in the repeats on the 5' side and 3' side as a result of recombination, and are therefore unlikely to be recognized by Cre recombinase, thus reducing the risk of causing a deletion mutation in the chromosome due to unwanted recombination. When the mutant loxP sequences lox71 and lox66 are used in combination, each may be placed on any of the 5' and 3' sides of the aforementioned vector component, but it is necessary that the mutant loxP sequences be inserted in an orientation such that the mutated sites would be located at the outer ends of the respective loxP sequences. 尚, While a preferable episomal vector in the present invention is an early-disappearing vector that falls off from the iPS cell in an early stage even without an action of Cre recombinase, since an exceptionally long time may be necessary for falling off from the cell, it may be preferable to design the loxP sequence to deal with the risk of unnecessary recombination and the like due to the treatment with Cre recombinase.

Each of the two loxP sequences is placed in the same orientation on the 5' and 3' sides of a vector constituent essential for the replication of episomal vector in a mammalian cell (i.e., replication origin functional in a mammalian cell (e.g., EBV oriP, SV40 on etc., preferably oriP), or a gene sequence that encodes a protein that binds to the replication origin to control the replication (e.g., EBNA-1, SV40 large T antigen etc., preferably EBNA-1)). The vector constituent flanked by the loxP sequences may be either a replication origin or a gene sequence that encodes a protein that binds to the replication origin to control the replication, or both.

The episomal vector to be used in the present invention provides not only the intrinsic effect of episomal vector that, whether or not the loxP sequence is present, an exogenous nucleic acid factor (including a reprogramming factor or a nucleic acid encoding an inhibitor of p53 function) constituting the vector is not incorporated into the cell genome even transiently when introduced into a somatic cell, but also an unexpected effect that the vector present as an episome falls off from the iPS cell in an early stage even without applying a Cre recombinase treatment. That is, the present invention also provides a self-disappearing episomal vector that provides the expression of reprogramming factor (s) and an inhibitor of p53 function sufficient for establishing an iPS cell, after which falls off from the cell in an early stage. As used herein, "fall off" means that the presence of the vector or expression of a reprogramming factor or an inhibitor of p53 function mounted on the vector is not detected (below detection limit) by the PCR analysis described in Example 6 or 10 or RT-PCR analysis described in Example 11 of WO 2011/016588 A1. Such vector is characterized in that it falls off from the iPS cell before 10 passages in 50% or more, preferably 60% or more, more preferably 70% or more, of the iPS cell clones established by the introduction of the vector. Alternatively, the self-disappearing episomal vector is characterized in that it is unstable in the cell to the degree that the copy number per $1\times10^4$ cells is in the order of $10^6$ within one week after introduction, whereas the copy number per $1\times10^4$ cells is 100 or less, preferably 50 or less, more preferably 30 or less, when the iPS cell is established (e.g., about 4 weeks from the vector introduction).

To be specific, the early-self-disappearing vector of the present invention has at least one, preferably 2 or more, more preferably 3 or more, particularly preferably 4 or more, structural characteristics of the following (i)-(vii).

(i) A loxP sequence is disposed in the same orientation on the 5'-side and 3'-side of a vector component necessary for replication of an episomal vector in a mammalian cell (e.g., EBNA-1 gene, SV40 Large T antigen gene, preferably EBNA-1 gene).

(ii) A nucleic acid encoding a reprogramming factor is under regulation of a CAG promoter.

(iii) A nucleic acid encoding a reprogramming factor or a dominant-negative mutant of p53 is under regulation of a CMV early-immediate enhancer.

(iv) A nucleic acid encoding a reprogramming factor or a dominant-negative mutant of p53 is under regulation of a rabbit β-globin polyA addition signal.

(v) A WPRE sequence is contained between a nucleic acid encoding a reprogramming factor or a dominant-negative mutant of p53 and a polyA addition signal.

(vi) A nucleic acid encoding p53 shRNA is under regulation of U6 promoter.

(vii) A replication origin (e.g., pUC ori, ColE1 ori, preferably pUC ori) functional in bacterium, and a marker gene (e.g., ampicillin resistant gene) that enables selection in bacterium are contained.

(viii) A vector component necessary for replication of an episomal vector in a mammalian cell (e.g., EBNA-1 gene, SV40 Large T antigen gene, preferably EBNA-1 gene) and a nucleic acid encoding each reprogramming factor or inhibitor of p53 function mounted on the vector are transcribed in the same orientation.

As shown in Example 6 of U.S. provisional patent application No. 61/521,153, an iPS cell can be established even when a transgene vector containing 4 expression cassettes on one episomal vector is introduced into a somatic cell. The establishment efficiency may be further improved by studying the order of expression cassettes also in this case.

(F) Extra EBNA-1 Vector Plasmid

In latent infection of cells with EBV (Epstein-Barr virus), EBNA-1 (Epstein-Barr virus nuclear antigen 1) protein plays an extremely important role in the replication and maintenance of its episome, and transcriptional expression of the virus gene group, and it is known that such function is achieved when said protein binds to the OriP region of the EBV genome DNA (Frappier, L., and O'Donnell, M. (1991) J. Biol. Chem. 266, 7819-7826). Extra EBNA-1 vector plasmid in the present invention utilizes such function of EBNA-1 and enables autonomous replication of an episomal vector having an OriP region. Extra EBNA-1 vector plasmid in the present invention carries a gene encoding EBNA-1 protein, and can transiently or constitutively express the EBNA-1 protein in a mammalian cell.

Any Extra EBNA-1 vector plasmid in the present invention is encompassed in the scope of the present invention as long as it is a plasmid having a structure containing an EBNA-1 coding region inserted under regulation of a promoter, and having a structure enabling the expression of the EBNA-1 coding region. For example, the Extra EBNA-1 vector plasmid in the present invention may contain, when desired, an enhancer, a polyA addition signal, a selection marker gene and the like in addition to the promoter. Examples of the selection marker gene include ampicillin resistant gene, dihydrofolate reductase gene, neomycin resistance gene, puromycin resistance gene and the like. As the promoter regulating the EBNA-1 coding region, EF1α promoter, CAG promoter, SRa promoter, SV40 promoter, LTR promoter, CMV (cytomegalovirus) promoter, RSV (Rous sarcoma virus) promoter, MoMuLV (moloney mouse leukemia virus) LTR, HSV-TK (simple herpes virus thymidine kinase) promoter and the like are used. Of these, CAG promoter, CMV promoter and the like are preferable. Extra EBNA-1 vector plasmid in the present invention can be produced, for example, using pCX-EGFP (FEBS Letters, 407, 313-319, 1997) and by the following steps.

WPRE sequence is inserted into the 5'-side of the pA sequence of pCX-EGFP, and SV40ori is further removed by a treatment with restriction enzyme BamHI.

Then, the EGFP part of the vector is removed by EcoRI, and EBNA-1 coding region is inserted instead.

The thus-obtained Extra EBNA-1 vector plasmid is also referred to as "pCXWB-EBNA-1" in the present specification.

In another embodiment, the Extra EBNA-1 vector plasmid in the present invention can be produced, for example, using pCX-EGFP (FEBS Letters, 407, 313-319, 1997) and by the following steps.

pCX-EGFP is treated with restriction enzyme BamHI to allow for self ligation (pCXB-EGFP).

Then, the vector is treated with restriction enzyme EcoRI, and EcoRI fragment of pCXWB-EBNA1 (EBNA-1 coding region) is inserted.

The thus-obtained Extra EBNA-1 vector plasmid is also referred to as "pCXB-EBNA1" in the present specification.

As a use embodiment of the Extra EBNA-1 vector plasmid, for example, it can be contacted with a cell in the iPS cell establishing step, simultaneously with an episomal vector carrying a nuclear reprogramming factor. In another embodiment, the Extra EBNA-1 vector plasmid can be contacted with a cell before or after contacting an episomal vector carrying a nuclear reprogramming factor with the cell. The former embodiment is more preferable for the enforcement of the present invention.

As the mechanism of iPS cell establishment efficiency improving effect of Extra EBNA-1 vector plasmid, for example, it may be considered that the amount of EBNA-1 bound to oriP is not sufficient by conventional methods, which in turn prevents sufficient replication of an episomal vector carrying an nuclear reprogramming factor, and causes insufficient expression level of the nuclear reprogramming factor; however, Extra EBNA-1 vector plasmid can compensate for the insufficient amount of EBNA-1. It is clear that the present invention is not affected at all even if the iPS cell establishment efficiency was indeed improved by some other mechanism.

In the present specification below, iPS cells established using an episomal vector is sometimes to be abbreviated as "epi-iPS cells" or "epi-iPSCs". When the combination of transgenes in the present invention is abbreviated as "C1, T1, T2, Y3, Y3+EBNA1, Y4, Y4+EBNA1, Y5+EBNA1, Y6+EBNA1", these combinations are as shown in the following Table 1.

TABLE 1

| Mixture name | Plasmid name | Amount (μg) | Genes |
|---|---|---|---|
| C1 | pEB-C5 | 2.5 | OCT3/4, SOX2, KLF4, c-MYC, LIN28 |
|  | pEB-Tg | 0.5 | SV40LT |
| T1 | pEP4EO2SEN2K | 1.05 | OCT3/4, SOX2, NANOG, KLF4 |
|  | pEP4EO2SET2K | 1.12 | OCT3/4, SOX2, SV40LT, KLF4 |
|  | pCEP4-M2L | 0.83 | C-MYC, LIN28 |
| T2 | pEP4EO2SET2K | 0.91 | OCT3/4, SOX2, SV40LT, KLF4 |
|  | pEP4EO2SCK2MEN2L | 2.09 | OCT3/4, SOX2, KLF4, c-MYC, NANOG, LIN28 |
| Y3 | pCXLE-hOCT3/4 | 1 | OCT3/4 |
|  | pCXLE-hSK | 1 | SOX2, KLF4 |
|  | pCXLE-hUL | 1 | L-MYC, LIN28 |
| Y3 + EBNA1 | pCXLE-hOCT3/4 | 0.83 | OCT3/4 |
|  | pCXLE-hSK | 0.83 | SOX2, KLF4 |
|  | pCXLE-hUL | 0.83 | L-MYC, LIN28 |
|  | pCXWB-EBNA1 | 0.5 | CAG::EBNA1 |
| Y4 | pCXLE-hOCT3/4-shp53 | 1 | OCT3/4, p53 shRNA |
|  | pCXLE-hSK | 1 | SOX2, KLF4 |
|  | pCXLE-hUL | 1 | L-MYC, LIN28 |
| Y4 + EBNA1 | pCXLE-hOCT3/4-shp53 | 0.83 | OCT3/4, p53 shRNA |
|  | pCXLE-hSK | 0.83 | SOX2, KLF4 |
|  | pCXLE-hUL | 0.83 | L-MYC, LIN28 |
|  | pCXWB-EBNA1 | 0.5 | CAG::EBNA1 |
| Y5 + EBNA1 (-WPRE) | pCE-hOCT3/4-shp53 | 0.83 | OCT3/4, p53 shRNA |
|  | pCE-hSK | 0.83 | SOX2, KLF4 |
|  | pCE-hUL | 0.83 | L-MYC, LIN28 |
|  | pCXB-EBNA1 | 0.5 | CAG::EBNA1 |
| Y6 + EBNA1 (-WPRE) (-shRNA) | pCE-hOCT3/4 | 0.625 | OCT3/4 |
|  | pCE-hSK | 0.625 | SOX2, KLF4 |
|  | pCE-hUL | 0.625 | L-MYC, LIN28 |
|  | pCE-mp53DD | 0.625 | mouse p53 dominant negative |
|  | pCXB-EBNA1 | 0.5 | CAG::EBNA1 |

(G) Method of Introducing Vector Set into Somatic Cell

A vector set composed of a combination of the above-mentioned episomal vectors can be introduced into somatic cells, for example, by using a lipofection method, a liposome method, an electroporation method, a calcium phosphate coprecipitation method, a DEAE dextran method, a microinjection method, a particle gun method and the like. Specifically, for example, the methods described in Science, 324: 797-801 (2009), WO 2011/016588 A1, Nature Methods, 8(5), 409-412 (2011) and the like can be used.

Whether a vector component necessary for replication of an episomal vector in a mammalian cell has been removed from iPS cells can be confirmed by performing Southern blot analysis or PCR analysis by using, as a probe or primer, a nucleic acid containing a base sequence in the vector component and/or a base sequence in the vicinity of loxP sequence when loxP sequence is used, and an episome fraction isolated from the iPS cells as a template, and examining the presence or absence of a band or the length of the detected band (see WO 2011/016588 A1, Nature Methods, 8(5), 409-412 (2011)). The episome fraction can be prepared by a method well known in the field and, for example, the methods described in Science, 324: 797-801 (2009), WO 2011/016588 A1, Nature Methods, 8(5), 409-412 (2011) and the like can be used.

(H) iPS Cell Establishment Efficiency Improving Substance

The establishment efficiency of iPS cell is expected to be further increased by contacting a known iPS cell establishment efficiency improving substance with a somatic cell. Examples of the iPS cell establishment efficiency improving substance include, but are not limited to, histone deacetylase (HDAC) inhibitor [e.g., valproic acid (VPA) (Nat. Biotechnol., 26(7): 795-797 (2008)), low-molecular-weight inhibitors such as trichostatin A, sodium butyrate, MC 1293, and M344, nucleic acid-based expression inhibitors such as siRNAs and shRNAs against HDAC (e.g., HDAC1 siRNA Smartpool® (Millipore), HuSH 29mer shRNA Constructs against HDAC1 (OriGene) and the like), and the like], G9a histone methyltransferase inhibitor [for example, nucleic acidic expression inhibitor such as low-molecular-weight inhibitors such as BIX-01294 (Cell Stem Cell, 2: 525-528 (2008)) and the like, siRNA and shRNA for G9a (e.g., G9a siRNA (human) (Santa Cruz Biotechnology) etc.) and the like, and the like], L-calcium channel agonist (for example, Bayk8644) (Cell Stem Cell, 3, 568-574 (2008)), UTF1 (Cell Stem Cell, 3, 475-479 (2008)), intracellular signal transduction regulator [for example, Wnt Signaling activator (for example, soluble Wnt3a) (Cell Stem Cell, 3, 132-135 (2008)), TGF-β inhibitor, MEK inhibitor, 2i/LIF (2i is inhibitor of mitogen-activated protein kinase signalling and glycogen synthase kinase-3, PloS Biology, 6(10), 2237-2247 (2008))], other natural or synthetic low-molecular-weight compound (e.g., 5'-azacytidine, thiazovivin, vitamin C etc.), ES cell specific miRNA (e.g., miR-302-367 cluster (Mol. Cell. Biol. doi:10.1128/MCB.00398-08, WO 2009/075119), miR-302 (RNA (2008) 14: 1-10), miR-291-3p, miR-294 and miR-295 (all of which Nat. Biotechnol. 27: 459-461 (2009))) and the like. As mentioned above, the nucleic acid-based expression inhibitors may be in the form of expression vectors harboring a DNA that encodes an siRNA or shRNA.

These iPS cell establishment efficiency improvers can be contacted with a somatic cell by a method similar to a conventional known method about the establishment efficiency improving factor of the present invention for each of (a) when the substance is a proteinous factor, (b) when the substance is a nucleic acid encoding the proteinous factor or (c) low-molecular-weight compound.

An iPS cell establishment efficiency improver may be contacted with a somatic cell simultaneously with the vector set of the present invention, and either one may be contacted in advance, as far as the iPS cell establishment efficiency from a somatic cell improves significantly compared with the efficiency obtained in the absence of the improver.

(I) Improving Establishment Efficiency by Culture Conditions

The iPS cell establishment efficiency can further be improved by culturing the cells under hypoxic conditions in the nuclear reprogramming process for somatic cells. As mentioned herein, the term "hypoxic conditions" means that the ambient oxygen concentration as of the time of cell culture is significantly lower than that in the atmosphere. Specifically, conditions involving lower oxygen concentrations than the ambient oxygen concentrations in the 5-10% $CO_2$/95-90% air atmosphere, which is commonly used for ordinary cell culture, can be mentioned; examples include conditions involving an ambient oxygen concentration of 18% or less. Preferably, the ambient oxygen concentration is 15% or less (e.g., 14% or less, 13% or less, 12% or less, 11% or less and the like), 10% or less (e.g., 9% or less, 8% or less, 7% or less, 6% or less and the like), or 5% or less (e.g., 4% or less, 3% or less, 2% or less and the like). The ambient oxygen concentration is preferably 0.1% or more (e.g., 0.2% or more, 0.3% or more, 0.4% or more and the like), 0.5% or more (e.g., 0.6% or more, 0.7% or more, 0.8% or more, 0.95% or more and the like), or 1% or more (e.g., 1.1% or more, 1.2% or more, 1.3% or more, 1.4% or more and the like).

Although any method of creating a hypoxic state in a cellular environment can be used, the easiest way is to culture cells in a $CO_2$ incubator permitting adjustments of oxygen concentration, and this represents a suitable case. $CO_2$ incubators permitting adjustment of oxygen concentration are commercially available from various manufacturers (e.g., $CO_2$ incubators for hypoxic culture manufactured by Thermo scientific, Ikemoto Scientific Technology, Juji Field, Wakenyaku etc.).

The time of starting cell culture under hypoxic conditions is not particularly limited, as far as iPS cell establishment efficiency is not prevented from being improved compared with the normal oxygen concentration (20%). Although the culture may be started before the somatic cell is contacted with the vector set of the present invention, or at the same time as the contact, or after the contact, it is preferable, for example, that the culture under hypoxic conditions be started just after the somatic cell is contacted with the vector set, or at a given time interval after the contact [e.g., 1 to 10 (e.g., 2, 3, 4, 5, 6, 7, 8 or 9) days].

The duration of cultivation of cells under hypoxic conditions is not particularly limited, as far as iPS cell establishment efficiency is not prevented from being improved compared with the normal oxygen concentration (20%); examples include, but are not limited to, periods of 3 days or more, 5 days or more, for 7 days or more or 10 days or more, and 50 days or less, 40 days or less, 35 days or less or 30 days or less and the like. Preferred duration of cultivation under hypoxic conditions varies depending on ambient oxygen concentration; those skilled in the art can adjust as appropriate the duration of cultivation according to the oxygen concentration used. In an embodiment of the present invention, if iPS cell candidate colonies are selected with drug resistance as an index, it is preferable that a normal oxygen concentration be restored from hypoxic conditions before starting drug selection.

Furthermore, preferred starting time and preferred duration of cultivation for cell culture under hypoxic conditions also vary depending on iPS cell establishment efficiency at normal oxygen concentrations and the like.

After being contacted with the vector set of the present invention (further iPS cell establishment efficiency improver where necessary), the cell can, for example, be cultured under conditions suitable for cultivation of ES cells. In the case of mouse cells, generally, the cultivation is carried out with the addition of leukemia inhibitory factor (LIF) as a differentiation suppression factor to an ordinary medium. Meanwhile, in the case of human cells, it is desirable that basic fibroblast growth factor (bFGF) and/or stem cell factor (SCF) be added in place of LIF. The cell may be cultured in the co-presence of, as feeder cells, mouse embryonic fibroblasts treated with radiation or an antibiotic to terminate the cell division, or may be cultured in a culture dish coated with an extracellular matrix instead of these feeder cells. As the mouse embryo-derived fibroblasts, generally, STO cell line (ATCC CRL-1503) and the like are often used as a feeder.

For induction of iPS cell, SNL cells obtained by stably incorporating neomycin resistance gene and LIF gene in STO cells (SNL76/7 STO cells; ECACC 07032801) (McMahon, A. P. & Bradley, A. Cell 62, 1073-1085 (1990)) and the like are often used. In addition, mouse embryo-derived primary fibroblasts (MEF) can also be used. Mitomycin C-treated MEF is commercially available from Millipore and ReproCELL Incorporated. Co-culture with these feeder cells may be started before contact with the vector set of the present invention, at the time of the contact, or after the contact (e.g., 1-10 days later).

The culture medium may contain a Rho kinase (ROCK) inhibitor. Particularly, when the culture step includes a step of dispersing human iPS cells in a single cell, it is preferable that the medium should contain a ROCK inhibitor. When MEF cells and SNL cells are used as a feeder cell, the medium used therefor may or may not contain a ROCK inhibitor, with preference given to the absence thereof. As the ROCK inhibitor, Y-27632 can be used, but the ROCK inhibitor is not limited thereto.

Using the vector set of the present invention, human iPS cell can be produced by culturing without the use of a non-human animal-derived component (i.e., under complete xeno-free conditions) from the introduction of the vector set into somatic cell to the establishment of iPS cell, and further to the maintenance as iPS cell. When human iPS cell is induced under xeno-free conditions, the vector set of the present invention (further, an iPS cell establishment efficiency improving substance as necessary) is contacted and the cells are cultured in a medium free of FCS and other non-human animal-derived components. As the substance (e.g., bFGF, SCF etc.) to be added to the medium as a differentiation inhibitor, human-derived purified protein, preferably a recombinant protein, is used. As the feeder cell, any human-derived somatic cells can be used. For example, human skin fibroblasts (HDF), human pulp stem cells and the like can be preferably used. It is also possible to induce human iPS cell without using a feeder cell. In this case, an extracellular matrix can also be used as a coating agent for a cell container. The extracellular matrix is a supramolecular structure present outside the cell, which may be naturally derived or an artificial product (recombinant). Examples thereof include substances such as collagen, proteoglycan, fibronectin, hyaluronic acid, tenascin, entactin, elastin, fibrillin and laminin, and fragments thereof. These extracellular substrates may be used in combination and may be, for example, prepared from the cells such as BD Matrigel (TM) and the like. Besides these, a commercially available xeno-free coating agent can be used. Examples of the commercially available xeno-free coating agent include, but are not limited to, CellStart, Coat1, VTN-N, Synthemax2, and Retronectin.

A method of establishing an iPS cell from peripheral blood mononuclear cells (T cell and non-T cell (including CD34 positive cell and stem, progenitor cells) by using an episomal vector is described in detail in, for example, Kyoto University iPS cell culture protocol (http://www.cira.kyoto-u.ac.jp/j/research/protocol.html).

A candidate colony of iPS cells can be selected in two ways: methods with drug resistance and reporter activity as indicators, and methods based on macroscopic examination of morphology. As an example of the former, a colony positive for drug resistance and/or reporter activity is selected using a recombinant cell wherein a drug resistance gene and/or a reporter gene is targeted to the locus of a gene highly expressed specifically in pluripotent cells (e.g., Fbx15, Nanog, Oct3/4 and the like, preferably Nanog or Oct3/4). Examples of such recombinant cells include MEFs derived from a mouse having the βgeo (which encodes a fusion protein of β-galactosidase and neomycin phosphotransferase) gene knocked in to the Fbx15 gene locus [Takahashi & Yamanaka, Cell, 126, 663-676 (2006)], and MEFs derived from a transgenic mouse having the green fluorescent protein (GFP) gene and the puromycin resistance gene integrated in the Nanog gene locus [Okita et al., Nature, 448, 313-317 (2007)]. Meanwhile, methods for selecting a candidate colony by macroscopic examination of morphology include, for example, the method described by Takahashi et al. in Cell, 131, 861-872 (2007). Although the methods using reporter cells are convenient and efficient, colony selection by macroscopic examination is desirable from the viewpoint of safety when iPS cells are prepared for therapeutic purposes in humans.

The identity of the cells of the selected colony as iPS cells can be confirmed by positive responses to Nanog (or Oct3/4) reporters (puromycin resistance, GFP positivity and the like), as well as by the visible formation of an ES cell-like colony, as described above; however, to ensure greater accuracy, it is possible to perform tests such as alkaline phosphatase staining, analyzing the expression of various ES-cell-specific genes, and transplanting the selected cells to a mouse and confirming teratoma formation.

The iPS cells thus established can be used for various purposes. For example, by utilizing a method of differentiation induction reported with respect to ES cells, differentiation into various cells (e.g., myocardial cells, blood cells, nerve cells, vascular endothelial cells, insulin-secreting cells and the like) from iPS cells can be induced. Therefore, inducing iPS cells using a somatic cell collected from a patient or another person of the same or substantially the same HLA type would enable stem cell therapy by autogeneic or allogeneic transplantation, wherein the iPS cells are differentiated into desired cells (that is, cells of an affected organ of the patient, cells that have a therapeutic effect on disease, and the like), which are transplanted to the patient. Furthermore, because functional cells (e.g., hepatocytes) differentiated from iPS cells are thought to better reflect the actual state of the functional cells in vivo than do corresponding existing cell lines, they can also be suitably used for in vitro screening for the effectiveness and toxicity of pharmaceutical candidate compounds and the like.

The present invention is hereinafter described in further detail by means of the following examples, to which, however, the scope of the present invention is not limited.

EXAMPLES

Example 1

Preparation of Various Episomal Plasmids to be Used for Reprogramming

Four kinds of plasmids (pCXLE-hOCT3/4, pCXLE-hSK, pCXLE-hUL and pCXLE-hOCT3/4-shp53-F) used were those produced before (Okita at al., Nature Methods, 8(5), 409-412(2011), WO 2011/016588). The outline of the constitution of the respective plasmids is as follows.

1) pCXLE-hOCT3/4 (Addgene#27076):

A plasmid wherein expression cassettes having a translation region of human Oct3/4 configured under regulation of CAG promoter (containing WPRE sequence and rabbit β-globin polyA addition signal at the downstream of the translational region, hereinafter the same) are configured in the 5' to 3' orientation in this order from the 3'-side of EBNA-1 gene (sense strand) as the origin (hereinafter the same).

2) pCXLE-hSK (Addgene#27078):

A plasmid wherein expression cassettes having a construct, wherein respective translational regions of human Sox2 and human Klf4 are linked via foot-and-mouth disease virus (FMV) 2A sequence (PLoS ONE 3, e2532, 2008, Stem Cells 25, 1707, 2007), disposed under regulation of CAG promoter are configured in the 5' to 3' orientation in this order from the 3'-side of EBNA-1 gene (sense strand) as the origin.

3) pCXLE-hUL (Addgene#27080):

A plasmid wherein expression cassettes having a construct, wherein respective translational regions of human L-Myc and human Lin28 are linked via foot-and-mouth disease virus (FMV) 2A sequence, disposed under regulation of CAG promoter are configured in the 5' to 3' orientation in this order from the 3'-side of EBNA-1 gene (sense strand) as the origin.

4) pCXLE-hOCT3/4-shp53-F (Addgene#27077):

A plasmid wherein expression cassettes having a nucleic acid region encoding p53shRNA and a translational region of human Oct3/4, which are disposed under regulation of U6 promoter and CAG promoter, respectively, are configured in the 5' to 3' orientation in this order.

pCEB-hSK-O, pCEB-hUL-G, pCE-EGFP, pCXLE-hG-LIS1, pCE-hOCT3/4, pCE-hOCT3/4-shp53-F, pCE-hSK, pCE-hUL and pCE-mp53DD were produced as follows.

1) pCEB-hSK-O:

WPRE sequence was inserted into the 5'-side of the pA sequence of pCX-EGFP (provided by Dr. Masaru OKABE, Osaka University, FEBS Letters, 407, 313-319, 1997), and further, SV40ori was removed by treating with restriction enzyme BamHI. This vector was pCXWB. The EGFP site of this vector was removed with EcoRI, and a translational region of human gene, which was cut out from pCXLE-hOCT3/4 with EcoRI in the same manner, was inserted instead. This was named pCXWB-hOCT3/4. This vector was treated with SalI, and pCXLE-hSK, which was treated with SalI in the same manner, was inserted thereinto to produce pCEB-hSK-O (FIG. 1A).

2) pCXLE-hGLIS1:

The hGLIS1 site of pMXs-hGLIS1 was amplified by PCR and inserted into pCR2.1. Then, an hGLIS1 fragment was cut out by treating with restriction enzyme EcoRI, and inserted into pCXLE-EGFP treated with restriction enzyme EcoRI.

3) pCEB-hUL-G:

The EGFP site of pCXWB was removed with EcoRI, and a translational region of human gene, which was cut out from pCXLE-hGLIS1 with EcoRI in the same manner, was inserted instead. This was named pCXWB-hGLIS1. This vector was treated with SalI, and pCXLE-hUL, which was treated with SalI in the same manner, was inserted thereinto to produce pCEB-hUL-G (FIG. 1B).

4) pCE-EGFP:

pBluescriptII KS– was treated with restriction enzymes BamHI/XhoI, and a linker was inserted thereinto to produce pBS-XhoBam. Then, pBS-XhoBam was treated with restriction enzymes SalI/MfeI, and a SalI/EcoRI fragment of pCEP4 was inserted thereinto to produce a pBS-CEP cassette. Then, pCX-EGFP was treated with restriction enzyme BamHI, and a BamHI/BglII fragment of pBS-CEP cassette was inserted thereinto to produce pCE-EGFP.

5) pCE-hOCT3/4 (FIG. 2A):

The above-mentioned pCE-EGFP was treated with restriction enzyme EcoRI, and an EcoRI fragment of pCXLE-hOCT3/4 was inserted thereinto.

6) pCE-hOCT3/4-shp53-F (FIG. 2B):

The above-mentioned pCE-hOCT3/4 was treated with restriction enzyme BamHI, and a BamHI fragment of pCXLE-hOCT3/4-shp53-F was inserted thereinto.

7) pCE-hSK (FIG. 2C):

The above-mentioned pCE-EGFP was treated with restriction enzyme EcoRI, and an EcoRI fragment of pCXLE-hSK was inserted thereinto.

8) pCE-hUL (FIG. 2D):

The above-mentioned pCE-EGFP was treated with restriction enzyme EcoRI, and an EcoRI fragment of pCXLE-hUL was inserted thereinto.

9) pCE-mp53DD (FIG. 2E):

The mp53DD site of pENTR-p53DD was amplified by PCR, and inserted into pCR2.1 to produce pTopo-mp53DD. Then, pCXLE-EGFP was treated with restriction enzyme EcoRI, and an EcoRI fragment of pTopo-mp53DD was inserted thereinto to produce pCXLE-mp53DD. Then, the above-mentioned pCE-EGFP was treated with restriction enzyme EcoRI, and an EcoRI fragment of pCXLE-mp53DD was inserted thereinto to produce pCE-mp53DD.

Example 2

Production of Extra EBNA-1 Vector Plasmid

Figure 3:
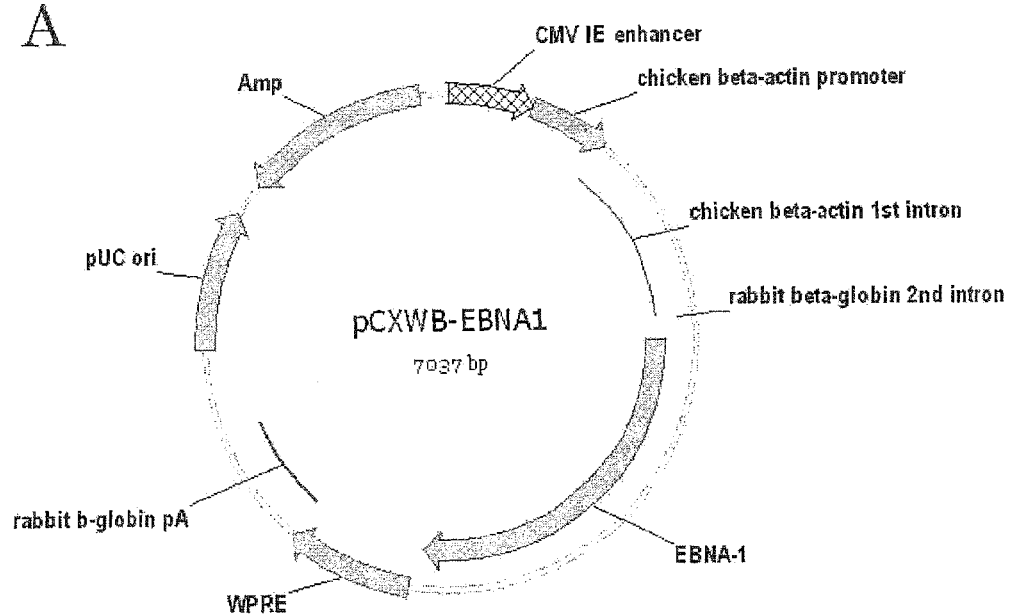
FIG. 3A shows the structure of Extra EBNA-1 vector plasmid (pCXWB-EBNA-1).
FIG. 3B shows the structure of Extra EBNA-1 vector plasmid (pCXB-EBNA-1).
Figure 3:
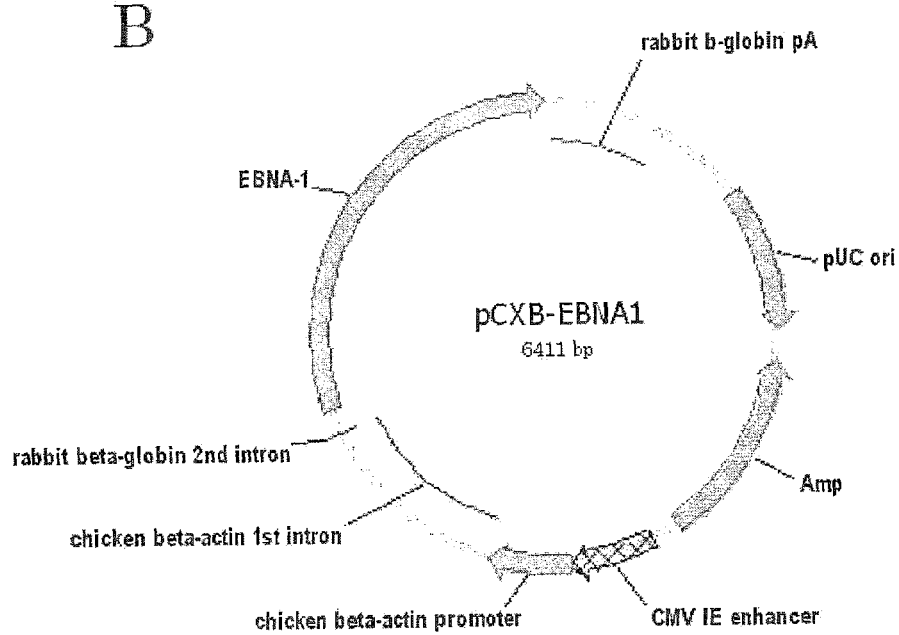

To express transgene efficiently, WPRE sequence was inserted into the 5'-side pA sequence of pCX-EGFP (provided by Dr. Masaru OKABE, Osaka University, FEBS Letters, 407, 313-319, 1997), and further SV40ori was removed by treating with restriction enzyme BamHI. This vector was pCXWB. Then, the EGFP site of pCXWB was removed with EcoRI, and an EBNA-1-coding region, which was amplified from pCEP4 (Invitrogen) by PCR, was inserted instead. This vector was named "pCXWB-EBNA1", and used in the following experiment (FIG. 3A).

pCXB-EBNA1, which is other Extra EBNA-1 vector plasmid, was produced as shown below. First, pCX-EGFP was treated with restriction enzyme BamHI to allow for self ligation. This vector was pCXB-EGFP. Then, pCXB-EGFP was treated with restriction enzyme EcoRI, and an EcoRI fragment of pCXWB-EBNA1 (EBNA-1coding region) was inserted to give pCXB-EBNA1 (FIG. 3B).

Example 3

Establishment of Human Fibroblast (HDF1419)-derived iPS Cell

Using a combination of plasmids (pCEB-hSK-O and pCEB-hUL-G), and a combination thereof with pCXWB-EBNA1, iPS cells were established from human fibroblast (HDF1419).

Figure 4:
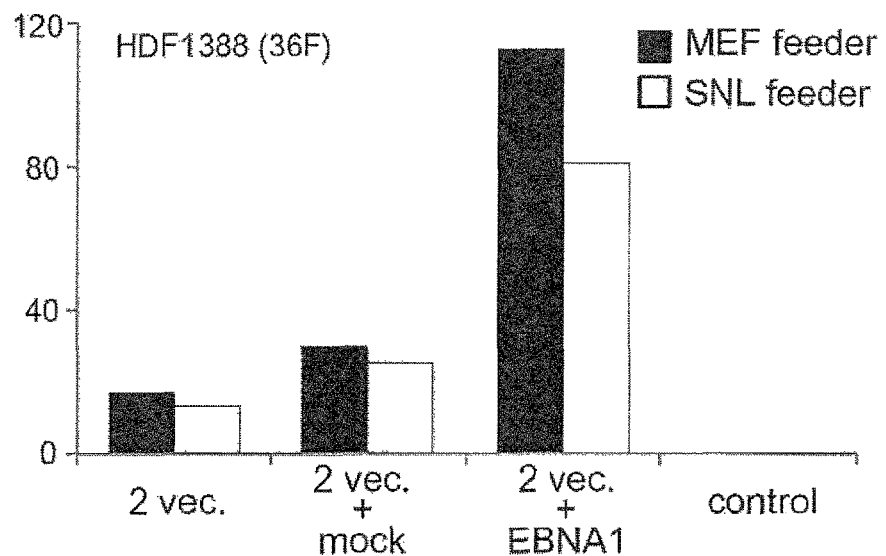
FIG. 4 shows establishment of iPS cell from human fibroblast (HDF1419). iPS cell was established from human fibroblast (HDF1419) by using 2 vec. (pCEB-hSK-O and pCEB-hUL-G) which is a combination of plasmids, and a combination thereof with pCXWB-EBNA1. As a feeder cell, mitomycin C-treated MEF, or mitomycin C-treated SNL was used.

Human fibroblasts (HDF1419) were purchased from Cell Applications, Inc. The fibroblasts were cultured and maintained in a culture medium (DMEM (Nacalai Tesque, Japan) supplemented with 10% fetal bovine serum (FCS, Invitrogen)) in a 100 mm culture dish at 37° C., 5% $CO_2$. For introduction of the plasmids, the medium was removed and PBS (5 mL) was added to wash the cells. PBS was removed, 0.25% Trypsin/1 mM EDTA (Invitrogen) was added, and the mixture was reacted at 37° C. for about 5 min. When the cells floated, DMEM/10% FCS was added to suspend the cells, and $6\times10^5$ cells were collected in a 15 mL centrifugation tube. The cells were centrifuged at 800 rpm for 5 min to remove the supernatant. Each plasmid (1.5 μg, pCXLE-hSK-O and pCEB-hUL-G) was introduced into the cells by a Microporator (ARBROWN CO., LTD.). The conditions for introduction were 100 μL chip, 1650 V, 10 ms and three pulses. The cells after the introduction were transferred into a 6 well culture plate (Falcon) previously added with DMEM/10% FCS (3 mL), and cultured under the conditions of 37° C., 5% $CO_2$ for 6 days. Thereafter, the medium was removed, and the cells were washed with PBS (2 mL). After removing PBS, 0.25% Trypsin/1 mM EDTA (Invitrogen) was added, and the mixture was reacted at 37° C. for about 5 min. When the cells floated, DMEM/10% FCS was added to suspend the cells, and $1 \times 10^5$ cells were plated on a 100 mm dish previously plated with feeder cells. As the feeder cell, mitomycin C-treated MEF or mitomycin C-treated SNL76/7 was used. The next day, the medium was exchanged with a medium for primate ES cell (ReproCELL Incorporated) added with bFGF (Wako) to 4 ng/mL, and thereafter, the medium exchange was continued every 2 days. On day 24 from the plasmid introduction, the numbers of ES-like colonies and non-ES-like colonies were counted, and the results are shown in FIG. 4.

It was clarified that the combined use of pCEB-hSK-O and pCEB-hUL-G with pCXWB-EBNA1 increases the iPS cell establishment efficiency.

Example 4

Establishment of Human Fibroblast (HDF1388)-derived iPS Cell

By a method similar to that in Example 3 and using plasmid combination Y4 (pCXLE-hOCT3/4-shp53-F, pCXLE-hSK and pCXLE-hUL) and a combination thereof with pCXWB-EBNA1, iPS cells were established from human fibroblasts (HDF1388).

Figure 5:
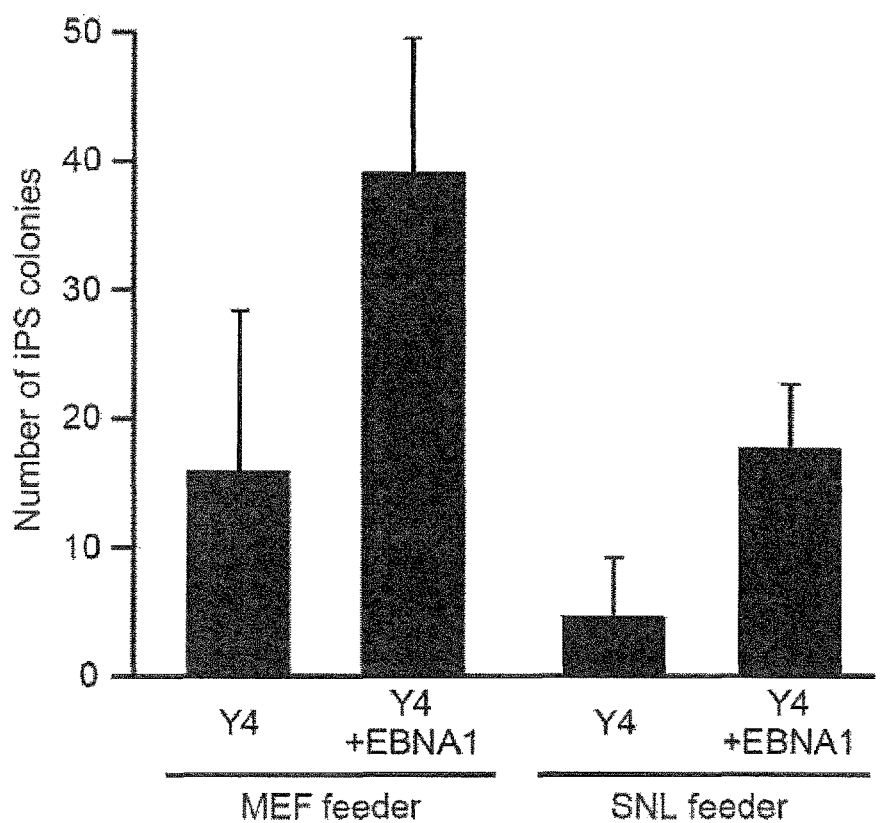
FIG. 5 shows establishment of iPS cell from human fibroblast (HDF1388). iPS cell was established from human fibroblast (HDF13889) by using Y4(pCXLE-hOCT3/4-shp53-F, pCXLE-hSK and pCXLE-hUL) which is a combination of plasmids, and a combination thereof with pCXWB-EBNA1. As a feeder cell, mitomycin C-treated MEF, or mitomycin C-treated SNL was used.

As a result, it was clarified that use of Y4 in combination with pCXWB-EBNA1 increases the iPS cell establishment efficiency (FIG. 5).

Example 5

Establishment of Human Peripheral Blood Mononuclear Cell (PMNC)-derived iPS Cell Using plasmid combination T2 (pEP4EO2SET2K and pEP4EO2SCK2MEN2L), Y3 (pCXLE-hOCT3/4, pCXLE-hSK and pCXLE-hUL) and Y4 (pCXLE-hOCT3/4-shp53-F, pCXLE-hSK and pCXLE-hUL), and a combination thereof with pCXWB-EBNA1, iPS cells were established from human peripheral blood mononuclear cells (PMNC).

Based on the guideline of Institutional Review Board, blood was collected from a health donor who gave an informed consent. PMNC was recovered from this blood by using Ficoll-paque Plus (GE Healthcare) or BD Vacutainer CPT (BD) and by the density gradient centrifugation method. Using NucleofectorII (Lonza), 3 μg of an expression plasmid mixture was introduced into $3-5 \times 10^6$ PMNCs. For introduction, Amaxa(R) Human T Cell Nucleofector(R) Kit was used. The cells after introduction were transferred into a 6 well culture plate (Falcon) previously plated with MEF feeder cells (mitomycin C-treated), and cultured under the conditions of 37° C., 5% $CO_2$. As the medium, X-vivo10 medium (Lonza) (for induction from T cell) added with 30 U/ml IL-2 (PeproTech) and 5 μl/well Dynabeads Human T-activator CD3/CD28, or αMEM medium added with 10% FCS, 10 ng/ml IL-3, 10 ng/ml IL-6, 10 ng/ml G-CSF and 10 ng/ml GM-CSF, or StemSpan H3000 (StemCell Technologies) (for induction from non-T cells) was used. On day 2 from plasmid introduction, without changing the medium, an equal amount of the medium for primate ES cell (ReproCELL Incorporated) added with 4 ng/mL bFGF and 10 μM Y27632 was added to each well. Then, on day 4 from plasmid introduction, the culture medium was exchanged with a medium for primate ES cell (ReproCELL Incorporated) added with 4 ng/mL bFGF and 10 μM Y27632. On day 20-25 from plasmid introduction, ES-like colonies (iPS cell colony) were counted.

Figure 6:
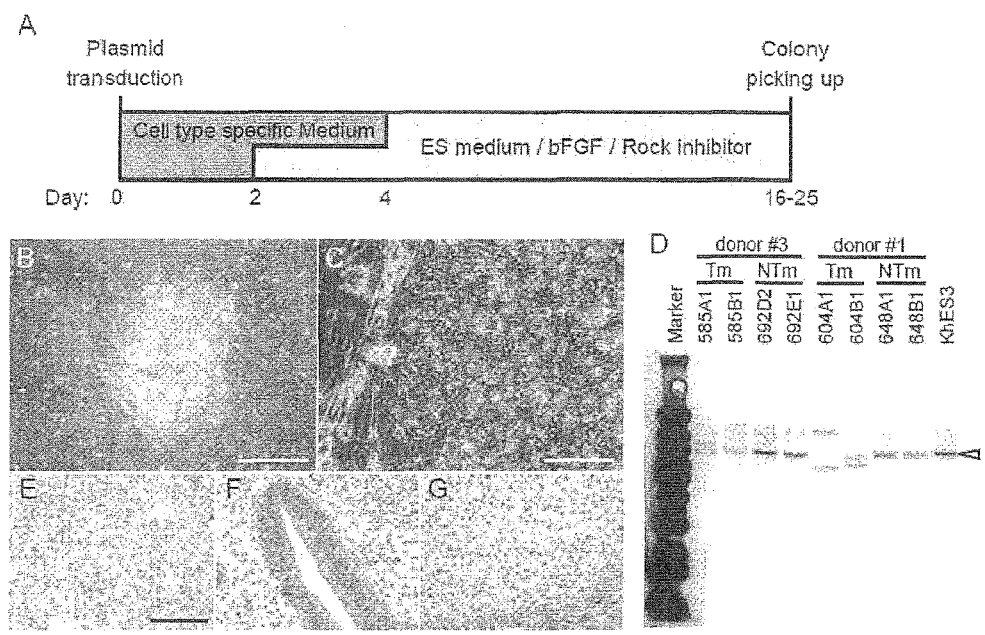
FIG. 6 shows establishment of iPS cell from human peripheral blood mononuclear cell (PMNC). (A) shows the protocol of iPS cell induction from PMNC using a plasmid. (B) and (C) are photographs of iPS cell colony established using plasmid combination Y4 (pCXLE-hOCT3/4-shp53-F, pCXLE-hSK and pCXLE-hUL). (D) shows the results of Southern blot analysis at TRB gene locus. V(D)J reknitting was found in the TRB gene locus of iPS cell clones (585A1, 585B1, 604A1 and 604B1) derived from two donors (#1 and #3). (E)-(G) show teratoma formation from iPS cells.
Figure 7:
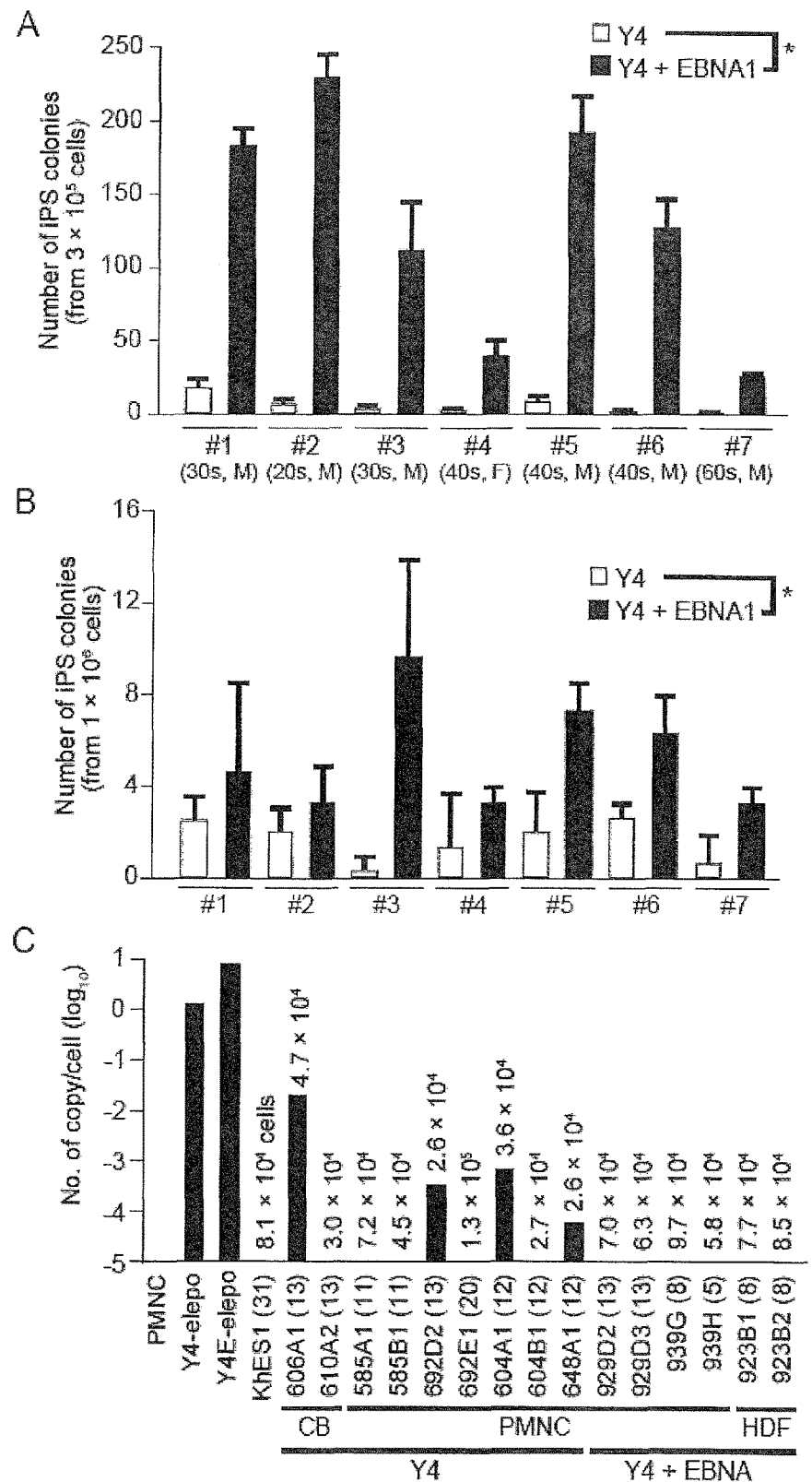
FIG. 7 shows an iPS cell establishment-promoting effect of Extra EBNA-1 vector plasmid. (A) and (B) show the results of iPS cell establishment from PMNC by using plasmid combination Y4 (pCXLE-hOCT3/4-shp53-F, pCXLE-hSK and pCXLE-hUL), and a combination thereof with pCXWB-EBNA1. As the medium, T cell medium (A) or non-T cell medium (B). (C) shows the number of copies of episomal vector remaining in the established iPS cells.

As a result, it was clarified that use of Y3 and Y4 in combination with pCXWB-EBNA1 increases the iPS cell establishment efficiency (FIGS. 6 and 7, Tables 2A and B). Similarly, it was clarified that use of a combination of Y5 (pCE-hOCT3/4-shp53, pCE-hSK and pCE-hUL), Y6 (pCE-hOCT3/4, pCE-hSK, pCE-hUL and pCE-mp53DD), and pCXB-EBNA1 successfully establishes iPS cells from PMNC (Table 2B), and use of a combination of Y5 and Y6 with pCXB-EBNA1 increases the iPS cell establishment efficiency. In addition, it was confirmed that, when a combination of Y6 and pCXB-EBNA1 is used, an iPS cell can also be established in the same manner by using a culture dish coated with 20 μg/ml RetroNectin (Takara) instead of MEF feeder cell.

TABLE 2

Table 2

A

Plasmid mixtures and conditions

| medium[a] | cell number ($\times 10^5$) | C1 (n = 3) | T1 (n = 3) | T2 (n = 6) | Y3 (n = 3) | Y3 + EBNA1 (n = 3) | Y4 (n = 6) | Y4 + EBNA1 (n = 3) | Y4 + EBNA1 with freezed PMNC (n = 3) |
|---|---|---|---|---|---|---|---|---|---|
| NTm | 10 | 0.0 ± 0.0 | 0.0 ± 0.0 | 0.0 ± 0.0 | 0.7 ± 0.6 | 1.3 ± 1.2 | 2.5 ± 1.0 | 4.7 ± 3.8 | 9.7 ± 2.1 |
|  | 3 | 0.0 ± 0.0 | 0.0 ± 0.0 | 0.0 ± 0.0 | 0.0 ± 0.0 | 0.7 ± 0.6 | 0.7 ± 0.8 | 4.3 ± 2.1 | 2.3 ± 1.2 |
| Tm | 10 | 0.0 ± 0.0 | 0.0 ± 0.0 | 0.0 ± 0.0 | 15.7 ± 8.1 | 51.7 ± 64.4 | 42.2 ± 8.4 | ND[b] | ND[b] |
|  | 3 | 0.0 ± 0.0 | 0.0 ± 0.0 | 0.0 ± 0.0 | 6.0 ± 3.5 | 9.0 ± 9.6 | 18.8 ± 6.1 | 184.0 ± 11.3 | 241.0 ± 77.7 |
|  | 1 | 0.0 ± 0.0 | 0.0 ± 0.0 | 0.0 ± 0.0 | 2.7 ± 2.1 | 5.3 ± 3.1 | 9.5 ± 2.7 | 82.7 ± 11.6 | 101.0 ± 26.5 |
|  | 0.3 | 0.0 ± 0.0 | 0.0 ± 0.0 | 0.0 ± 0.0 | 0.3 ± 0.6 | 0.7 ± 1.2 | 1.2 ± 0.8 | 19.3 ± 9.6 | 31.3 ± 12.9 |

Note:
[a]NTm, medium for non-T cell population; Tm, medium for T cells.
[b]ND, not determined because of too many colony formation.

TABLE 2-continued

Table 2

| | B | | | |
|---|---|---|---|---|
| | cell | Plasmid mixtures and conditions | | |
| medium[a] | number (×10$^5$) | Y4 + EBNA1 (n = 1) | Y5 + EBNA1 (n = 1) | Y6 + EBNA1 (n = 1) |
| Tm | 10 | ND | 184 | 268 |
| | 3 | 242 | 43 | 145 |
| | 1 | 66 | 9 | 46 |
| | 0.3 | 64 | 8 | 18 |

Note:
[a]Tm, medium for T cells.
[b]ND, not determined because of too many colony formation.

Since the present invention can strikingly increase the establishment efficiency of iPS cell, human iPS cell can be provided more efficiently. According to the present invention, moreover, since iPS cell can be efficiently established from blood cells, which was extremely difficult by conventional methods, the present invention is extremely useful for the application of human iPS cell to regenerative medicine.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

The contents described in any publication cited herein, including patents and patent applications, are hereby incorporated in their entireties by reference, to the extent that they have been disclosed herein.

This application is based on U.S. provisional patent application No. 61/650,694 (filing date: May 23, 2012, the contents of which are encompassed in full herein.

The invention claimed is:

1. A method of producing a human iPS cell, comprising a step of introducing the following (1) and (2):

(1) one or more episomal vectors containing a nucleic acid encoding a nuclear reprogramming factor, oriP, and a nucleic acid encoding EBNA-1; and (2) a plasmid vector containing a nucleic acid encoding EBNA-1 and not containing oriP into a human somatic cell, thereby producing a human iPS cell.

2. The method according to claim 1, further comprising introducing a nucleic acid, encoding an inhibitor of p53 function, in the form of an episomal vector.

3. The method according to claim 2, wherein the inhibitor of p53 function is p53 shRNA or a dominant negative mutant of p53.

4. The method according to claim 3, wherein the dominant negative mutant of p53 is p53DD.

5. The method according to claim 1, wherein the nuclear reprogramming factor is one or more selected from the group consisting of the members of Oct family, Klf family, Sox family, Myc family, Lin family and Glis family.

6. The method according to claim 5, wherein the nuclear reprogramming factors are Oct3/4, Klf4, Sox2, L-Myc and Lin28.

7. The method according to claim 6, wherein the nuclear reprogramming factors are Oct3/4, Klf4, Sox2, L-Myc, Lin28 and Glis1.

8. The method according to claim 1, wherein the nucleic acid encoding a nuclear reprogramming factor is divided and contained in 2 or 3 episomal vectors.

9. The method according to claim 1, wherein the episomal vectors containing the nucleic acid encoding a nuclear reprogramming factor are the following (1) or (2):

(1) pCEB-hSK-O and pCEB-hUL-G or (2) pCXLE-hOCT3/4, pCXLE-hSK and pCXLE-hUL.

10. The method according to claim 2, wherein the episomal vectors containing the nucleic acid encoding a nuclear reprogramming factor are pCXLE-hOCT3/4-shp53-F, pCXLE-hSK and pCXLE-hUL.

11. The method according to claim 2, wherein the episomal vectors containing the nucleic acid encoding a nuclear reprogramming factor are pCE-hOCT3/4-shp53, pCE-hSK and pCE-hUL.

12. The method according to claim 2, wherein the episomal vectors containing the nucleic acid encoding a nuclear reprogramming factor are pCE-hOCT3/4, pCE-hSK and pCE-hUL, and the episomal vector containing the nucleic acid encoding an inhibitor of p53 function is pCE-mp53DD.

13. The method according to claim 9, wherein the plasmid vector containing the nucleic acid encoding EBNA-1 is pCXWB-EBNA1.

14. The method according to claim 10, wherein the plasmid vector containing the nucleic acid encoding EBNA-1 is pCXB-EBNA1.

15. The method according to claim 1, wherein the somatic cell is selected from human fibroblast (HDF) and human blood cell.

16. The method according to claim 15, wherein the blood cell is a peripheral blood mononuclear cell (PMNC).

17. The method according to claim 16, wherein the peripheral blood mononuclear cell (PMNC) is a T cell.

18. A method of producing a human iPS cell, comprising a step of introducing the following (1) and (2):
   (1) one or more episomal vectors containing a nucleic acid encoding a nuclear reprogramming factor, oriP, and a nucleic acid encoding EBNA-1; and
   (2) a plasmid vector containing a nucleic acid encoding EBNA-1 and not containing a replication origin functional in a mammalian cell
into a human somatic cell, thereby producing a human iPS cell.

19. The method of claim 18, wherein the plasmid vector of (2) does not contain a nucleic acid encoding a nuclear reprogramming factor.

20. The method of claim 1, wherein the plasmid vector of (2) does not contain a nucleic acid encoding a nuclear reprogramming factor.

\* \* \* \* \*

SEQUENCE LISTING

<160> NUMBER OF SEQ ID NOS: 1

<210> SEQ ID NO 1
<211> LENGTH: 48
<212> TYPE: DNA
<213> ORGANISM: Artificial sequence
<220> FEATURE:
<223> OTHER INFORMATION: Synthetic shRNA against p53

<400> SEQUENCE: 1
gactccagtg gtaatctact gctcgagcag tagattacca ctggagtc        48